(12) United States Patent
Charbonnet

(10) Patent No.: US 7,767,404 B2
(45) Date of Patent: Aug. 3, 2010

(54) APPARATUS AND METHOD FOR SINGLE-STEP IMMUNOSORBENT ASSAY FOR SINGLE AND MULTIPLE ANALYTES

(75) Inventor: Derrick Charbonnet, Ocean Springs, MS (US)

(73) Assignee: Chipotle Business Group, Inc., Arlington, TX (US)

( * ) Notice: Subject to any disclaimer, the term of this patent is extended or adjusted under 35 U.S.C. 154(b) by 0 days.

(21) Appl. No.: 11/506,178

(22) Filed: Aug. 16, 2006

(65) Prior Publication Data

US 2007/0042430 A1 Feb. 22, 2007

Related U.S. Application Data

(60) Provisional application No. 60/708,459, filed on Aug. 16, 2005, provisional application No. 60/708,576, filed on Aug. 16, 2005, provisional application No. 60/709,268, filed on Aug. 18, 2005.

(51) Int. Cl.
*G01N 33/53* (2006.01)
(52) U.S. Cl. ....................................... 435/7.1
(58) Field of Classification Search ............... 435/287.2, 435/287.1, 287.3, 287.9, 288, 288.4, 288.7; 436/524, 518
See application file for complete search history.

(56) References Cited

U.S. PATENT DOCUMENTS

| | | | | |
|---|---|---|---|---|
| 5,270,164 A | * | 12/1993 | Anderson et al. | 435/6 |
| 5,281,540 A | * | 1/1994 | Merkh et al. | 436/530 |
| 5,281,541 A | * | 1/1994 | Saito et al. | 438/4 |
| 6,027,946 A | * | 2/2000 | Weitschies et al. | 436/526 |
| 6,388,788 B1 | * | 5/2002 | Harris et al. | 359/196.1 |
| 6,730,521 B1 | * | 5/2004 | Cassells | 436/523 |
| 7,494,776 B2 | * | 2/2009 | Wallace et al. | 435/6 |
| 2005/0014171 A1 | * | 1/2005 | Fraser et al. | 435/6 |
| 2005/0124008 A1 | * | 6/2005 | Kauvar | 435/7.9 |
| 2006/0057635 A1 | * | 3/2006 | Mansson et al. | 435/7.1 |
| 2006/0166296 A1 | * | 7/2006 | Nishii et al. | 435/7.92 |
| 2007/0020713 A1 | * | 1/2007 | Saini et al. | 435/7.92 |
| 2007/0292966 A1 | * | 12/2007 | Prickett et al. | 436/501 |

* cited by examiner

*Primary Examiner*—Ann Y Lam
(74) *Attorney, Agent, or Firm*—Kammer Browning PLLC

(57) ABSTRACT

The present invention discloses an apparatus and method for minimizing or eliminating steps in immunosorbent assays by eliminating both the need to attach target molecules to the test well and the need to remove unbound antibodies through rinsing. The single-step immunosorbent assay (SISA) includes the step of mixing the immunologic molecules with the sample and detection. SISA is utilized for a single analyte or target. The present invention further discloses a single-step immunosorbent assay for multiple analytes (SISAMA) for testing a plurality of analytes or targets in a single well using a modified SISA test wherein different fluorescent tags are attached to different antibody pairs. The present invention further includes various types of cassettes having test wells for the rapid and simultaneous testing of fluids for a plurality of components. Embodiments of this invention uniquely utilize colorimetric reagent reactions for ease of testing.

2 Claims, 18 Drawing Sheets

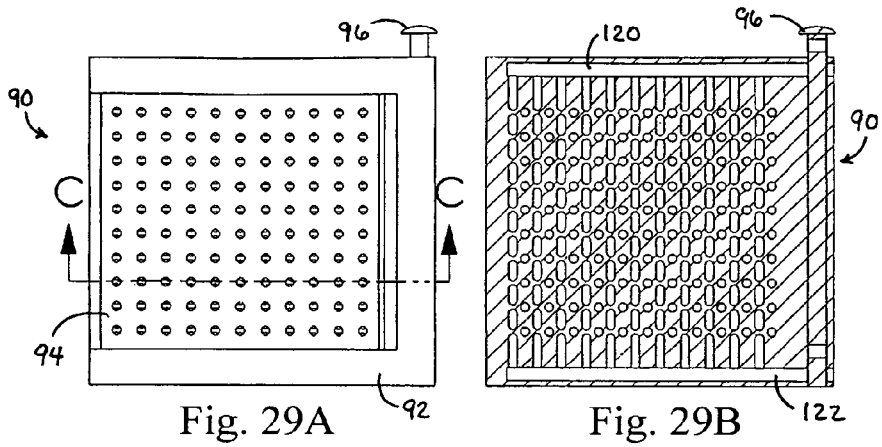
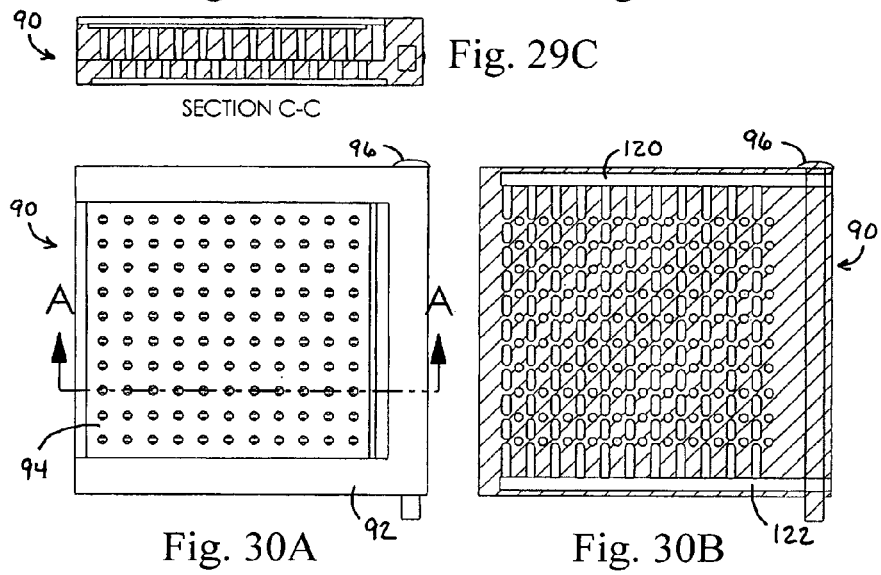
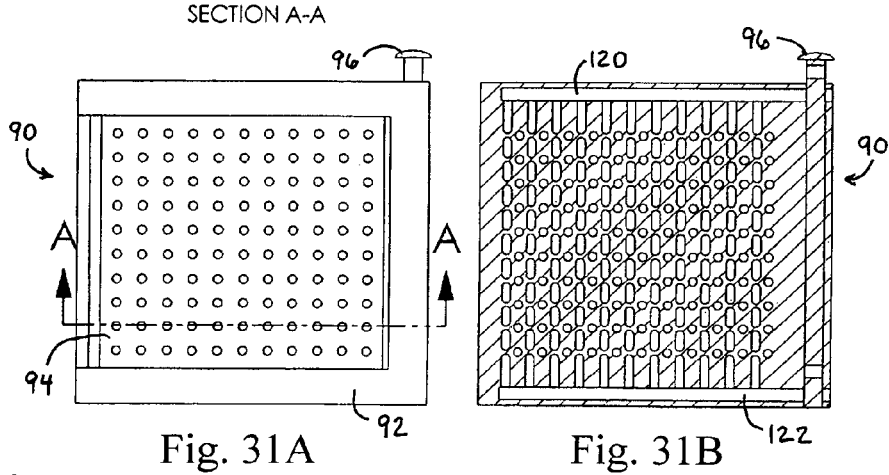

US 7,767,404 B2

APPARATUS AND METHOD FOR SINGLE-STEP IMMUNOSORBENT ASSAY FOR SINGLE AND MULTIPLE ANALYTES

CROSS REFERENCE TO CORRESPONDING APPLICATIONS

This application claims the benefit under Title 35 United States Code §119(e) of U.S. Provisional Application No. 60/708,459 filed Aug. 16, 2005; U.S. Provisional Application No. 60/708,576 filed Aug. 16, 2005; and U.S. Provisional Application No. 60/709,268 filed Aug. 18, 2005, the full disclosures of which are incorporated herein by reference.

BACKGROUND OF THE INVENTION

A vast number of biomolecules and biological entities (such as proteins and other complex molecules, and bacteria, fungal cells and other cell types) can be detected using immunologic techniques. Common among these tests, and well-known in the art, are ELISA (Enzyme-Linked ImmunoSorbent Assay) tests. Typically an ELISA test's target (the antigen) has molecular properties for which binding domains of antibodies have affinity. Antibodies are molecules that "fit" and bind to the antigen; the binding can be strong or weak. In order to identify those biomolecules and biological entities that are bound by specific antibodies, a tag (in this case, an enzyme) is typically attached to the antibodies. These tags react with additional chemical markers that, after enzymatic catalysis, fluoresce or cause the solution to change color. Other immunologic tests use radioactive tags (e.g., radioimmuno assay, or RIA, tests).

All of these immunologic tests require multiple steps. In an ELISA test, for example, a first step is to attach target entities to a test well. A second step is to introduce a fluid containing tagged antibodies into the well. The tagged antibodies then bind with considerable specificity to matching antigens (and less so, or not at all, to the other entities that may be present in the well). After fluid is removed, the test well is rinsed to remove unbound antibodies (if a detection step is prematurely implemented before rinsing, all antibodies, whether tightly bound to antigen or unbound, may potentially be detected). Finally, the well is refilled with a neutral fluid and marker chemicals are added. A detection step is then implemented, and the presence or amount of antigen is determined from a color change or florescence measurement. A reliable and efficient means of minimizing or eliminating steps in immunosorbent assays is needed.

Testing of a liquid sample often requires manually adding a liquid reagent to the liquid sample followed by manually mixing the liquid sample and the added liquid reagent. For example, in order to test a liquid sample, a researcher may add, through the use of a micropipette, a liquid reagent to an aliquot of the liquid sample in a microtube. The researcher may then need to mix the liquid sample with the added liquid reagent by further repetitively drawing up and expelling the mixture from the micropipette into the microtube. User variability (e.g., that may result from fatigue on the part of the researcher) or method variability introduced by relying on such micropipette-based mixing may adversely effect the reliability of subsequent measurements (e.g., colorimetric readings of chemical reactions in the liquid mixture).

The mixing of liquids is accomplished in some methods of high throughput screening (e.g., utilizing standard 96-well, 384-well, 1536-well or 3456-well plates) through automated additions of liquids across rows of wells within plates. These high throughput screening methods, however, generally require extensive electromechanical equipment and computer programming support for implementation. A generally simpler system for effecting the simultaneous mixing of a plurality of liquids is often needed.

SUMMARY OF THE INVENTION

Some of the embodiments of the present invention are directed to the analysis of a single analyte in an immunosorbent assay, while other embodiments of the present invention are directed to the analysis of multiple analytes or targets per well in an immunosorbent assay. All of the embodiments of the present invention provide means of minimizing or eliminating steps in immunosorbent assays. The step of mixing the immunologic molecules with the sample and then accomplishing detection remain, thus resulting in Single-step ImmunoSorbent Assay (SISA). A reduction in steps is accomplished primarily by eliminating the need for two steps: 1) attaching target molecules to the well, and 2) removing unbound antibodies through rinsing. This assay is utilized for a single analyte or target.

The embodiments of the invention directed to a test for a plurality of analytes or targets in a single well use a modified SISA test, thus resulting in Single-step ImmunoSorbent Assay for Multiple Analytes (SISAMA). A primary means of detecting multiple analytes (or multiple targets) in embodiments of SISAMA is by attaching different fluorescent tags (e.g., tags that fluoresce at different wavelengths of light) to different antibody pairs.

The present invention further includes various types of cassettes having test wells for the rapid and simultaneous testing of fluids for a plurality of components. Embodiments of this invention utilize colorimetric reactions of reagents in a unique way for the easy performance of such testing. This summary of the invention is not intended to represent each embodiment or every aspect of the present invention.

BRIEF DESCRIPTION OF THE DRAWINGS

A more complete understanding of the method and apparatus of the present invention may be obtained by reference to the following Detailed Description when taken in conjunction with the accompanying Drawings, wherein:

FIGS. 29A-29C diagram this second embodiment of a cassette for testing fluids in a closed, ready-to-use position. The air outlet port and runner (at the top of the cassette and plunger) are not aligned, and neither is the water or sample inlet port and runner (at the bottom of the cassette and plunger). The cassette is in a sealed, closed, ready to use position. The holes in the front and back pieces are not aligned and the reagent is captured in the back piece. This section view shows the air outlet runner (at top) and the water inlet runner (at bottom) are cut off by the plunger;

FIGS. 30A-30C diagram this second embodiment of a cassette for testing fluids in a sample-taking position. Both the air outlet port and runner (at the top of the cassette and plunger) and the water or sample inlet port and runner (at the bottom of the cassette and plunger) are aligned. Consequently, water or sample from the cassette's exterior can fill wells in the inner or front plate with water or sample fluid. But the reagent wells or reagent well portions in the outer sleeve or back plate are not aligned with wells or well portions of water or sample in the cassette's inner or front plate. Consequently, reagent remains captured in the outer sleeve or back plate. The holes in the front and back are not aligned and the reagent remains captured in the back piece. With the plunger depressed, the air outlet runner (at top) and the water inlet runner (at bottom) are now open to the sample media. This allows the sample wells in the front piece to fill with the sample fluid;

FIGS. 31A-31C diagram this second embodiment of a cassette for testing fluids in an analysis position. The trigger or plunger has returned to its original position (again, the air outlet port and runner at the top of the cassette and plunger are not aligned, and neither are the water or sample inlet port and runner at the bottom of the cassette and plunger), and water or sample fluid has been captured in the cassette. When a researcher or an operator is ready to proceed with sample analysis, the researcher or operator may snap or shift the inner or front plate so that the reagent wells or reagent well portions of the outer sleeve or back plate align, or connect, with the wells or well portions of water or sample in the inner or front plate (to the right in this view). This changes the alignment of the wells from the sampling runners to being aligned with the reagent wells. A small bubble left in the reagent wells causes complete mixing when the cassette is shaken (yet stays out of the way in the wide part of the sample well to allow clear detection through the now complete well by the detector);

DETAILED DESCRIPTION OF THE PREFERRED EMBODIMENTS

Figure 1:
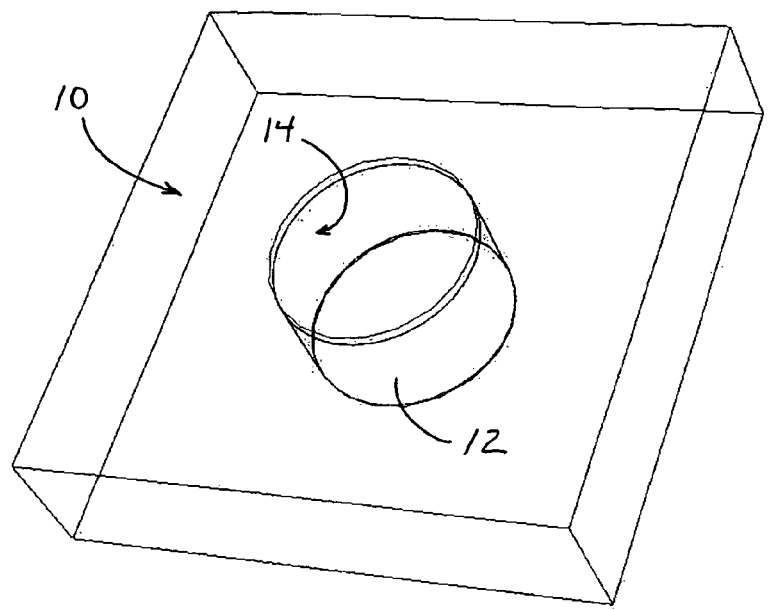
FIG. 1 is a test well with scavenger antigens.

As summarized above, the present invention is directed to an apparatus and method for single-step immunosorbent assay for single and multiple analytes. The present invention includes the following components: a single-step immunosorbent assay for a single analyte, a single-step immunosorbent assay for multiple analytes, and various cassette structures for testing fluids and methods of use in immunosorbent assays.

Single-Step Immunosorbent Assay for a Single Analyte

Embodiments of this invention make use of florescent tags (or other tags that react specifically to light or other electromagnetic energy). For example, instead of target entities being bound to the well, a second antigen (the "scavenger antigen") that is similar to the antigen in question is obtained or prepared and bound to the well. In embodiments of the invention, this scavenger antigen is bound only to the walls of the well, not the bottom. In other embodiments, scavenger antigens may be bound only to the bottom of a well (and the detection light beam shone through clear well sides so as to limit or avoid illumination of the well bottom). The antibodies bind to scavenger antigen but with less affinity or avidity than to target molecules. In some embodiments, the number of scavenger antigens considerably exceeds the number of antibodies.

In other configurations of the invention, the diameter of the well is larger than the diameter of the light beam used for detection. After the antibody solution is added to the well, the target solution is added, and the well is agitated. The antibodies present bind to either the targets, which are largely suspended in solution, or the scavenger antigens on the well walls. In further aspects, there must be enough time and agitation to ensure that all the antibodies are bound either to the targets or the scavenger antigens.

In further embodiments, a detection light beam, either a laser or another tightly focused beam, is then shone through the well. In some embodiments, the walls of the well are out of the path of the detection light or the walls are shaped in such a way as to cast shadows in order to prevent or minimize the detection beam's striking the tagged antibodies bound to scavenger antigen on the walls. When the detection light beam shines into the well, it strikes the targets suspended in solution within the well and not the antibodies bound to the walls. Thus in these embodiments, only the florescence from the antibodies bound to targets is detected. In addition to being shone through the well, the beam can be absorbed or reflected off the well bottom in other embodiments. The emissions from the tagged antibodies can be detected from the top, bottom, or any convenient direction in various embodiments.

In another embodiment, the scavenger antigens are attached to items or carriers that float or remain suspended in the fluid of the well. These items or carriers have holes within which shadow areas are created and within which the scavenger antigens attach.

In another embodiment, wells having perpendicular ridges along their side wall are utilized, and scavenger antigen is attached along the inside of these ridges. The ridges can shadow tagged antibodies bound to scavenger antigen and prevent light emissions from these tagged antibodies from otherwise contaminating detection measurements.

In another embodiment, radioactive tags are used with wells that have sufficient shadowing elements to prevent stray radiation from disrupting detection of radioactivity from tagged antibodies bound to target molecules.

Figure 2:
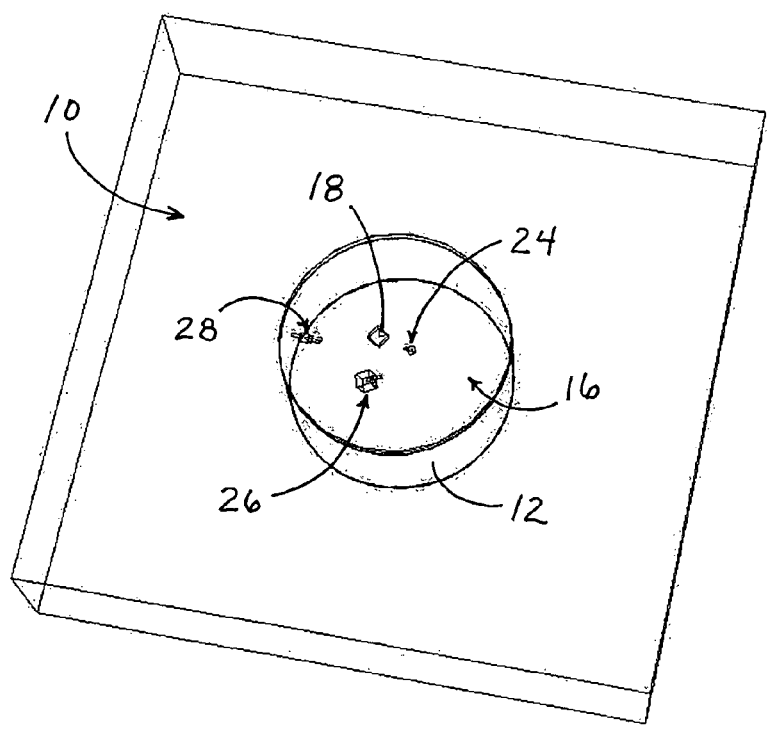
FIG. 2 is a test well with target fluid added.
Figure 3:
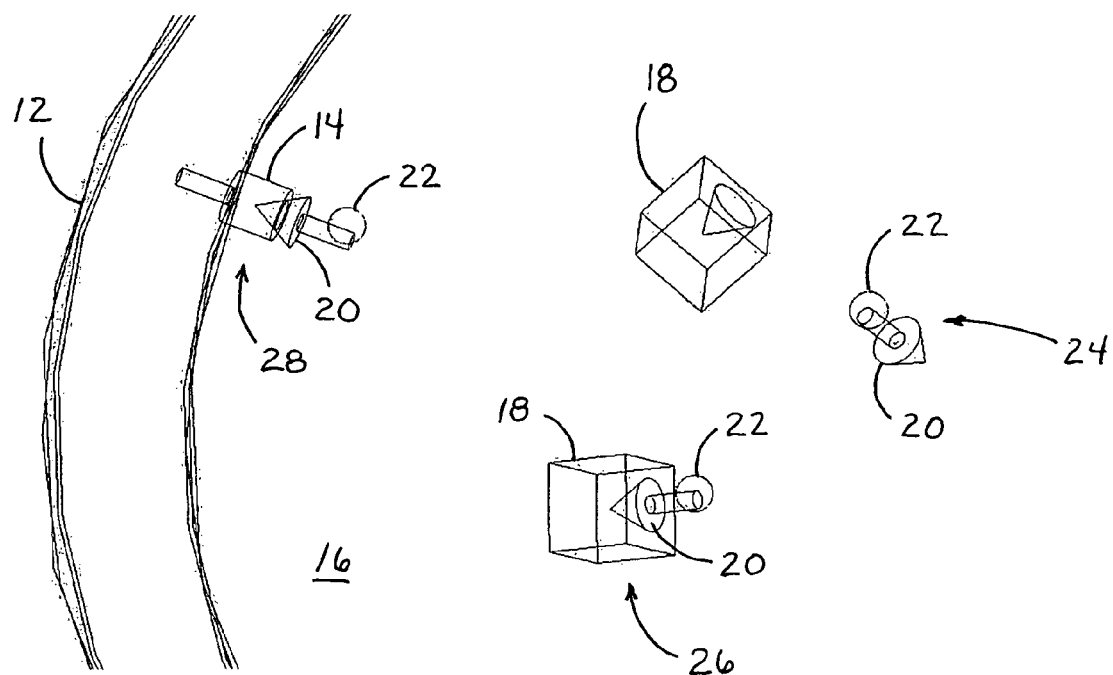
FIG. 3 is a model of antibodies (cones) and antigens (cubes: targets; cylinders: scavenger antigens)
Figure 4:
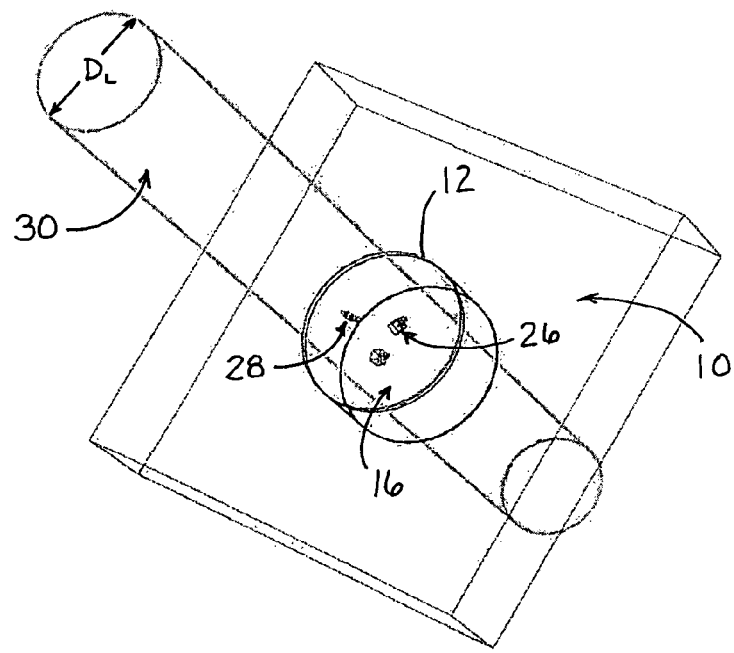
FIG. 4 is a test well through which a detection light beam passes.
Figure 5:
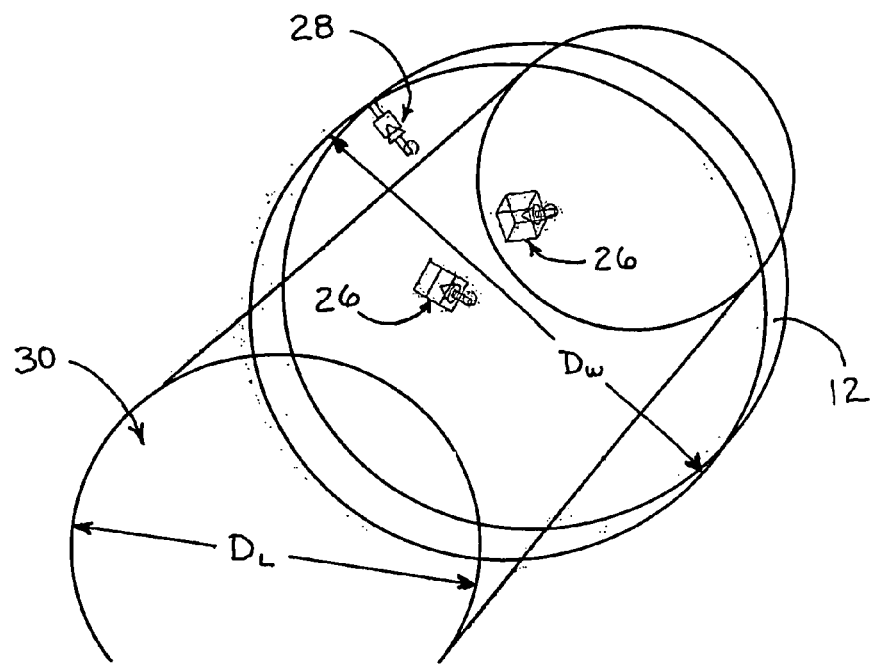
FIG. 5 illustrates a test well with a detection light detecting target antigens and not detecting scavenger antigen.
Figure 6:
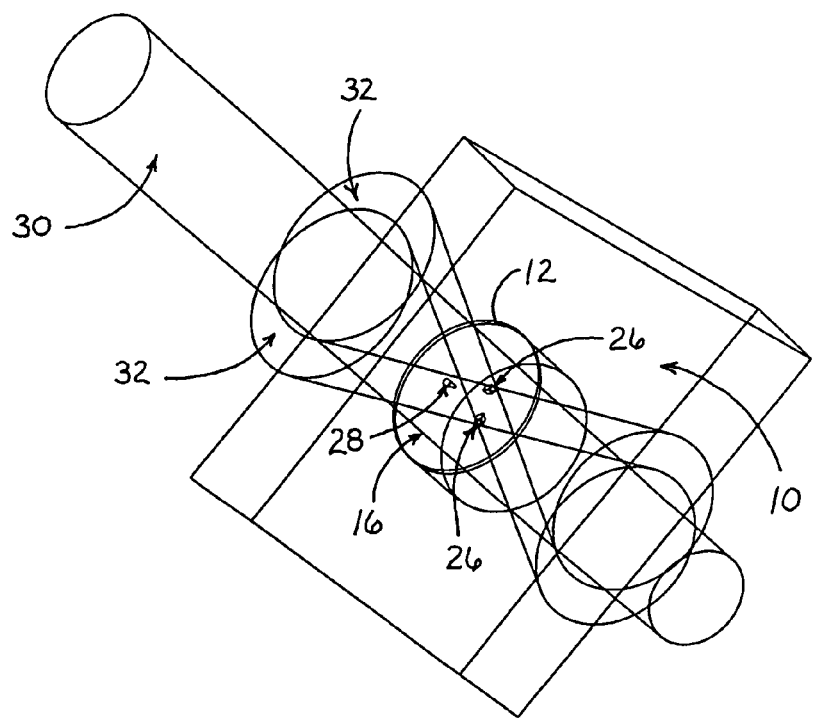
FIG. 6 illustrates a test well containing tags in solution within the well fluorescing and tags attached to scavenger antigens not fluorescing.

FIG. 1 is a test well 10 with well wall 12 and scavenger antigens 14. FIG. 2 is a test well with target fluid 16 added. Also shown in FIG. 2 are target antigen 18, antibody with tag 24, target antigen bound to antibody with tag 26, and scavenger antigen bound to antibody with tag 28. FIG. 3 is a model of antibodies (cones) 20 and antigens (cubes: targets 18; cylinders: scavenger antigens 14), and tags (spheres) 22. FIG. 4 is a test well 10 through which a detection light beam 30 passes. FIG. 5 illustrates a test well 10 of diameter $D_W$ with a detection light 30 of diameter $D_L$ detecting target antigens 18 and not detecting scavenger antigen 14. FIG. 6 illustrates a test well 10 containing target antigen bound to antibody with tag 26 in solution within the well fluorescing 32 and antibody with tag attached to scavenger antigen 28 not fluorescing.

These and other embodiments include characteristics noted in Table 1.

TABLE 1

Single Analyte Methodology Features

| No. | Description of Characteristics of Embodiments |
|---|---|
| 1 | Detection is accomplished with a beam of electromagnetic energy or radiation. The beam is shielded, focused, lased, or controlled in some way so as specifically to avoid illumination of areas where scavenger antigens are located. |
| 2 | Scavenger antigen is obtained or prepared has a lower binding affinity or avidity with the antibody than the target antigen has with the antibody in order to ensure that the antibodies preferentially bind to the targets. |
| 3 | Scavenger antigen is bound to a portion of the well that is not illuminated by the detection beam but the antibody-containing test solution yet contacts that portion of the well. |
| 4 | The scavenger antigen may be bound to items floating or suspended in the well, but these items have holes, pits, etc., that shadow tagged antibodies that bind to the scavenger antigen. |
| 5 | Antibody is obtained or prepared that binds tightly to the target antigen. |
| 6 | Antibody is conjugated with a tag that fluoresces or radiates when struck by the detection beam. The resulting fluorescence or radiation is detected by devices inside or outside the well. |
| 7 | The tagged antibody is capable of being dissolved or suspended in the test fluid. |
| 8 | The detection beam can be switched on and off, and yet the signal from the |

TABLE 1-continued

Single Analyte Methodology Features

No. Description of Characteristics of Embodiments tagged antibody can be detected during the off periods.
9  The detection beam can be continuous, and yet the signal from the tagged tagged antibody can be detected as an additional signal.
10 The detection of the signal from tagged antibodies can be accomplished from a range of angles.
11 The well has lips that provide additional shadow area to shield the scavenger antigen from the detection beam.
12 The well has ridges on its walls that provide additional shadow area to shield the scavenger antigen from the detection beam.
13 The well has depressions or holes that provide additional shadow area to shield the scavenger antigen from the detection beam.
14 The well bottom does not reflect or scatter the detection beam back into the well.
15 The test fluid surface may be flat and does not act as a lens.
16 The test fluid surface may be made flat by contact with a well top.
17 The test fluid surface may be made flat by avoiding surface tension differences between the fluid and the well.
18 The test fluid surface may be made flat by filling the well exactly to the neutral fill volume between the meniscus above and below the top of the well.

Single-Step Immunosorbent Assay for Multiple Analytes

As described above, embodiments of SISA make use of florescent tags (or other tags that react specifically to light or other energy). In embodiments of SISA for example, instead of target entities being bound to the well, a second antigen (the "scavenger antigen") that is similar to the antigen in question is obtained or prepared and bound to the well. In embodiments of SISA, this scavenger antigen is bound only to the walls of the well, not the bottom. In other embodiments of SISA, scavenger antigens may be bound only to the bottom of a well (and the detection light beam shone through clear well sides so as to limit or avoid illumination of the well bottom); the antibodies (i.e., SISA antibodies) bind to scavenger antigen but with less affinity or avidity than to target molecules. In some embodiments of SISA, the number of scavenger antigens considerably exceeds the number of antibodies (i.e., SISA antibodies).

In other configurations of SISA, the diameter of the well is larger than the diameter of the light beam used for detection. Furthermore, after the antibody solution (i.e., the solution containing SISA antibody) is added to the well, the target solution is added, and the well is agitated; the antibodies (i.e., SISA antibodies) present bind to either the targets, which are largely suspended in solution, or the scavenger antigens on the well walls. In further aspects of SISA, there must be enough time and agitation to ensure that all the antibodies (i.e., SISA antibodies) are bound either to the targets or the scavenger antigens.

In further embodiments of SISA, a detection light beam, either a laser or another tightly focused beam, is then shone through the well. In some embodiments of SISA, the walls of the well are out of the path of the detection light or the walls are shaped in such a way as to cast shadows in order to prevent or minimize the detection beam's striking the tagged antibodies that are bound to the wall (i.e., tagged SISA antibodies) that, being in excess over target molecules in solution, are bound to scavenger antigen on the walls. When the detection light beam shines into the well, it strikes the targets suspended in solution within the well and not the antibodies (i.e., not the tagged SISA antibodies) bound to the walls. Thus in these embodiments of SISA, only the florescence from the antibodies (i.e., tagged SISA antibodies) bound to targets is detected. In addition to being shone through the well, the beam can be absorbed or reflected off the well bottom in other embodiments of SISA. The emissions from the tagged antibodies can be detected from the top, bottom, or any convenient direction in various embodiments of SEA.

In another embodiment of SISA, the scavenger antigens are attached to items or carriers that float or remain suspended in the fluid of the well. These items or carriers have holes within which shadow areas are created and within which the scavenger antigens attach.

In another embodiment of SISA, wells having perpendicular ridges along their side wall are utilized, and scavenger antigen is attached along the inside of these ridges. The ridges can shadow tagged antibodies (i.e., excess SISA antibodies) bound to scavenger antigen and prevent light emissions from these tagged antibodies from otherwise contaminating detection measurements.

In another embodiment of SISA, radioactive tags are used with wells that have sufficient shadowing elements to prevent stray radiation from disrupting detection of radioactivity from tagged antibodies (i.e., SISA antibodies) bound to target molecules. Embodiments of SISA are further described in the provisional U.S. patent application entitled "Single-step ImmunoSorbent Assay" filed Aug. 16, 2005 (serial no. not yet assigned), which, as previously noted, is incorporated by reference herein in its entirety.

Embodiments of SISA and embodiments of SISAMA share fundamental characteristics. As in embodiments of SISA, for example, embodiments of SISAMA make use of florescent tags (or other tags that react specifically to light, other energy, or radioactivity). In embodiments of SISAMA, however, a second antibody (scavenger antibody) is obtained or prepared. Furthermore, unlike in embodiments of SISA, scavenger antigen in embodiments of SISAMA is matched to scavenger antibody but not to target antibody. Binding between scavenger antibody and scavenger antigen is generally of a lower affinity or avidity than the binding between primary antibody and target molecule in embodiments of SISAMA.

In embodiments of SISAMA, primary antibody and scavenger antibody are conjugated as an antibody pair (i.e., a SISAMA antibody pair), and, additionally, a tag is attached to the SISAMA antibody pair. In embodiments of SISAMA, scavenger antigen binds to scavenger antibody but with less affinity or avidity than primary antibody binds to a target molecule or intended analyte. In preferred embodiments, many more scavenger antigens are present than SISAMA antibody pairs (i.e., pairs of primary antibody conjugated to scavenger antibody).

In embodiments of SISAMA, the scavenger antibody and the target antibody are conjugated in such a way that they both cannot or do not bind to their respective antigens at the same time.

In embodiments of SISAMA, primary antibody species or kinds are in one-to-one correspondence with species or kinds of targets or analytes for which testing is to be accomplished. That is, in embodiments of SISAMA, a primary antibody species or kind of a SISAMA antibody pair only cross-reacts or binds with high affinity or avidity to one species or kind of target or analyte. Furthermore, in embodiments of the invention, each primary antibody species or kind (e.g., of a SISAMA antibody pair) has an identifying tag (e.g., one that fluoresces at a specific wavelength, or responds to, or emits, a specific type of radiation).

As in embodiments of SISA, scavenger antigen is attached to the sides of a well in embodiments of SISAMA. Binding of scavenger antibody (e.g., of a SISAMA antibody pair) to scavenger antigen attached to a well wall is thus facilitated in embodiments of SISAMA. In further embodiments of SISAMA, mixtures of SISAMA antibody pairs (i.e., various pairs wherein, for example, the primary antibody that is conjugated to scavenger antibody may differ for each antibody pair type) may be added to a solution within the well so that a different primary antibody type or kind of a SISAMA antibody pair mixture matches to specific types or kinds of target molecules that are added to the well. In embodiments of SISAMA, each type or kind of SISAMA antibody pair is identifiable by the type or kind of tag that is attached to the primary antibody of each SISAMA antibody pair.

In embodiments of SISAMA, when a well solution containing SISAMA antibody pairs is agitated or otherwise allowed to incubate, the various conjugated primary antibodies of the SISAMA antibody pairs bind to the various matching target molecules; all SISAMA antibody pairs that do not bind (via their conjugated primary antibody component) to targets in solution bind (via their opposite conjugated scavenger antibody component) to the scavenger antigen attached to well walls. As a result, in embodiments of SISAMA, only tagged SISAMA antibody pairs that are bound to targets remain floating or suspended in the well solution.

In further embodiments of SISAMA, a detection light beam, a laser, or another tightly focused beam, is then shone through the well. In some embodiments of SISAMA, the walls of the well are out of the path of the detection light or the walls are shaped in such a way as to cast shadows to prevent or minimize the detection beam's striking the tagged SISAMA antibody pairs bound to scavenger antigen on the walls. When the detection light beam shines into the well, it strikes the tagged SISAMA antibody pair-bound targets floating or suspended in solution within the well, but the detection light beam does not strike the tagged SISAMA antibody pairs bound to scavenger antigen that is attached to the walls. Thus in these embodiments of SISAMA, only the florescence from the tagged SISAMA antibody pairs bound to targets floating or suspended in solution is detected. The intensity of specific florescence wavelengths (or other characteristics used to distinguish tagged SISAMA antibody pairs that bind to a different analyte or target species or kinds) can be used to quantify the levels of analyte or other target floating or suspended in the well.

In addition to being shone through the well, the beam can be absorbed or reflected off the bottom in other embodiments of SISAMA. Emissions from the tagged SISAMA antibody pairs can be detected from the top, bottom, or any convenient direction in various embodiments.

Fluorescing radiation from tagged SISAMA antibody pairs bound to analytes or targets shines from the well to the detectors in embodiments of SISAMA; the detector has the capacity to distinguish signals that are simultaneously transmitted but that differ or vary based on the tagged SISAMA antibody pair from which a signal originated. Again, in embodiments of SISAMA, specific tagged SISAMA antibody pairs bind (via their conjugated primary antibody component) to specific target molecules. In some SISAMA embodiments, the fluorescing radiation or light shines into a spectroscopic analyzer. This device, well known in the art, spreads the light out in the manner of a prism and then uses a photosensitive device (such as a photosensitive charge-coupled device or CCD) to convert radiation spectra into electrical or digital signals specific for each of the different tags. In embodiments of SISAMA, the strength of an electrical or digital signal specific for a tag is proportional to the concentration of analyte or target suspended in the well.

In another embodiment of SISAMA, the scavenger antigens are attached to items or carners that float or remain suspended in the fluid of the well. These items or carners have holes within which shadow areas are created and within which the scavenger antigens attach.

In another embodiment of SISAMA, wells having perpendicular ridges along their side wall are utilized, and the scavenger antigen is attached along the inside of these ridges. The ridges can shadow tagged SISAMA antibody pairs bound to scavenger antigen and prevent light emissions from these tagged SISAMA antibody pairs from otherwise contaminating detection measurements.

In another embodiment, radioactive tags are used in place of, or in addition to, fluorescent tags on SISAMA antibody pairs with wells that have sufficient shadowing elements to prevent stray radiation from disrupting detection of radioactivity from tagged antibodies bound to analyte or target molecules.

Figure 7:
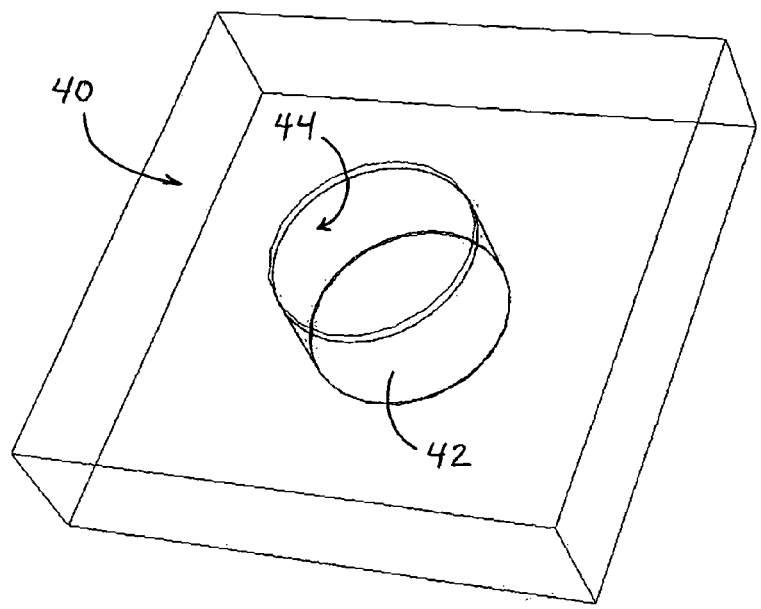
FIG. 7 is a well with scavenger antigens.
Figure 8:
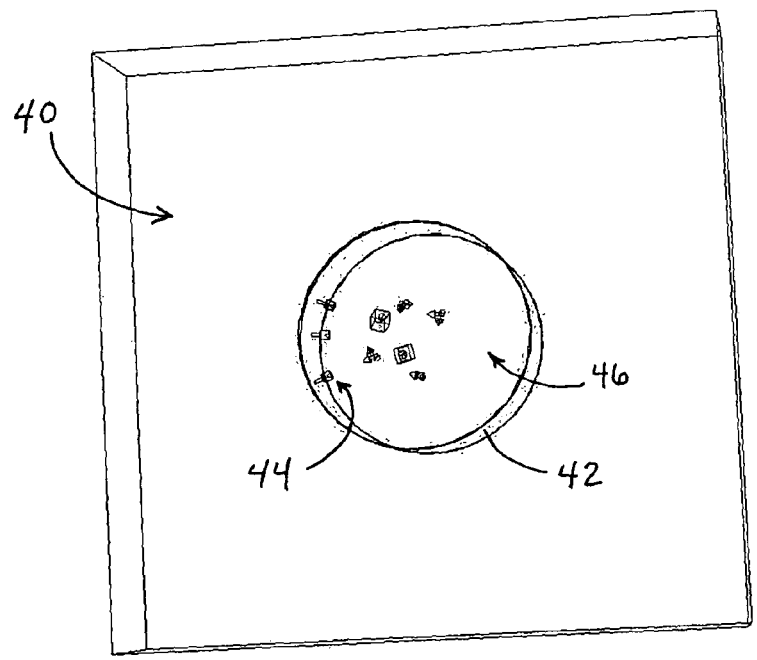
FIG. 8 is a well with target fluid added having targets and antibody pairs suspended or floating freely in the solution.
Figure 9:
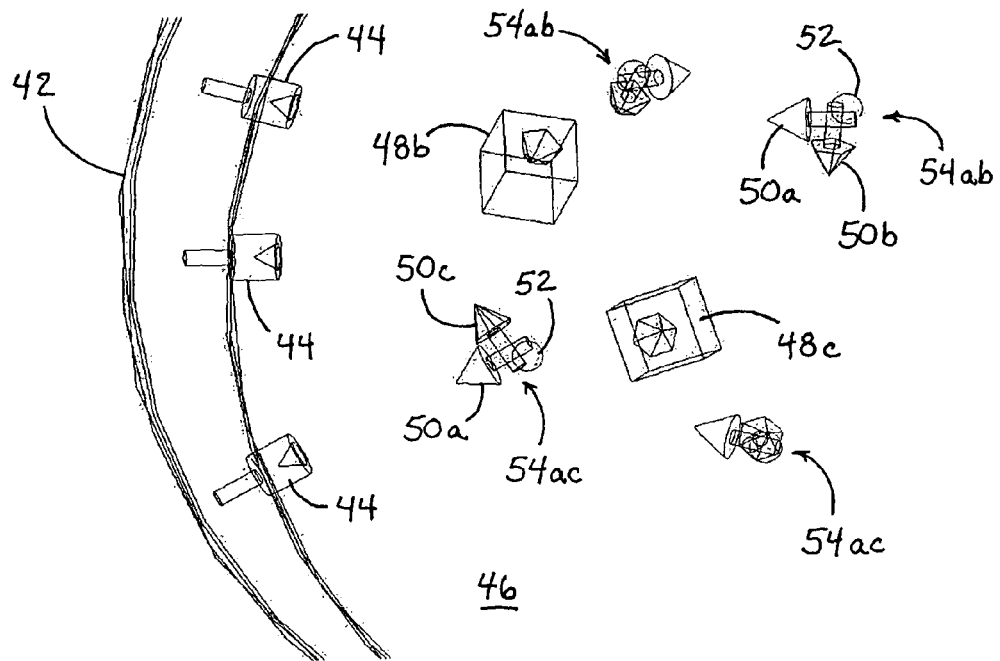
FIG. 9 is a model of SISAMA antibody pairs (tagged cone pairs) and antigens (cubes: targets; cylinders: scavenger antigens). Two types of tagged antibody pairs and two types of targets are depicted (the two types of tagged antibody pairs differ in the type of primary or target antibody that is conjugated with scavenger antibody in each tagged antibody pair)
Figure 10:
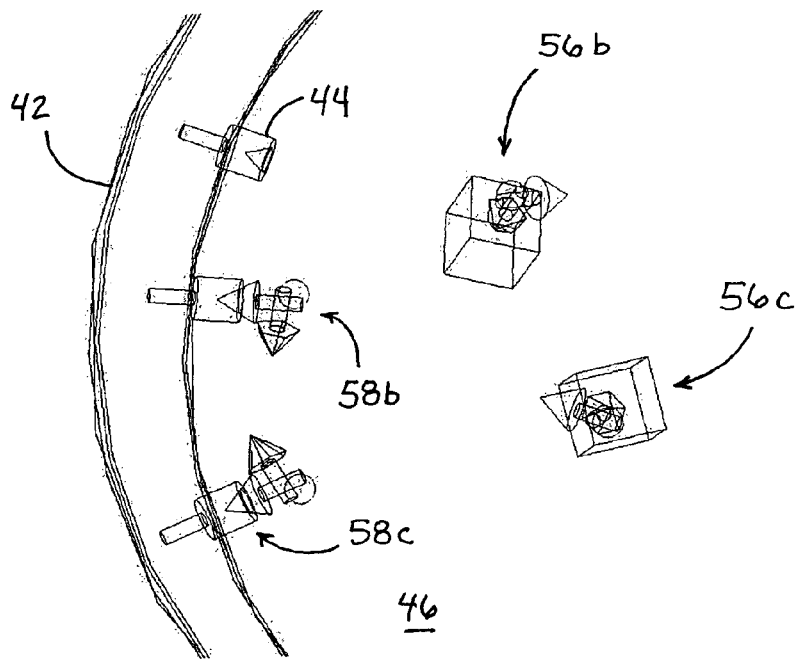
FIG. 10 illustrates four SISAMA antibody pairs (one of two SISAMA antibody pairs that is suspended in solution is bound to one type of target, and the other of two SISAMA antibody pairs that is suspended in solution is bound to another type of target; two of the four SISAMA antibody pairs are in excess and are bound to scavenger antigens attached to the well wall). Each of the two depicted targets is appropriately bound by a corresponding SISAMA antibody pair, and each of the two depicted excess SISAMA antibody pairs is bound (via its scavenger antibody) to scavenger antigen attached to the well wall.
Figure 11:
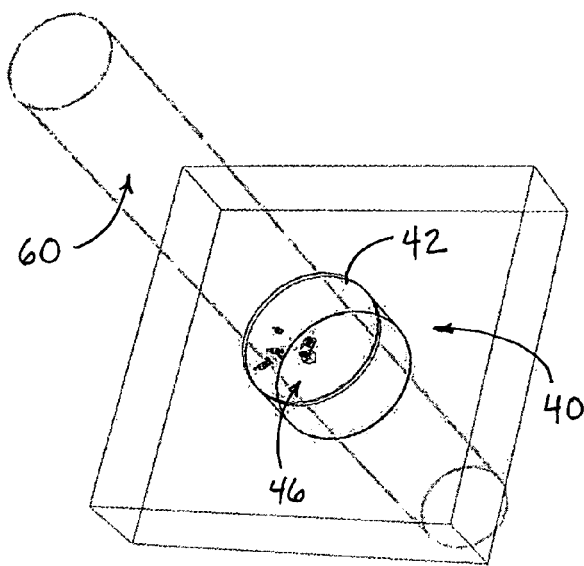
FIG. 11 is a well through which a detection light passes.
Figure 12:
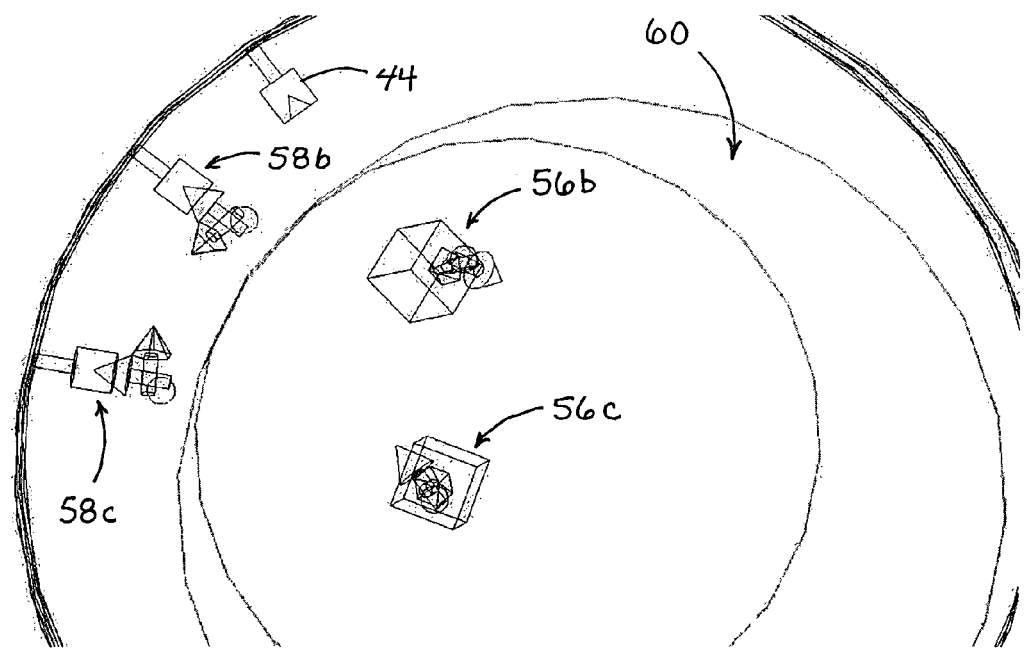
FIG. 12 illustrates detection light missing scavenger antigen (detection light also is missing two tagged SISAMA antibody pairs bound to scavenger antigen; detection light is also illustrated as illuminating each of two tagged SISAMA antibody pairs, each of which is bound to a different target antigen)
Figure 13:
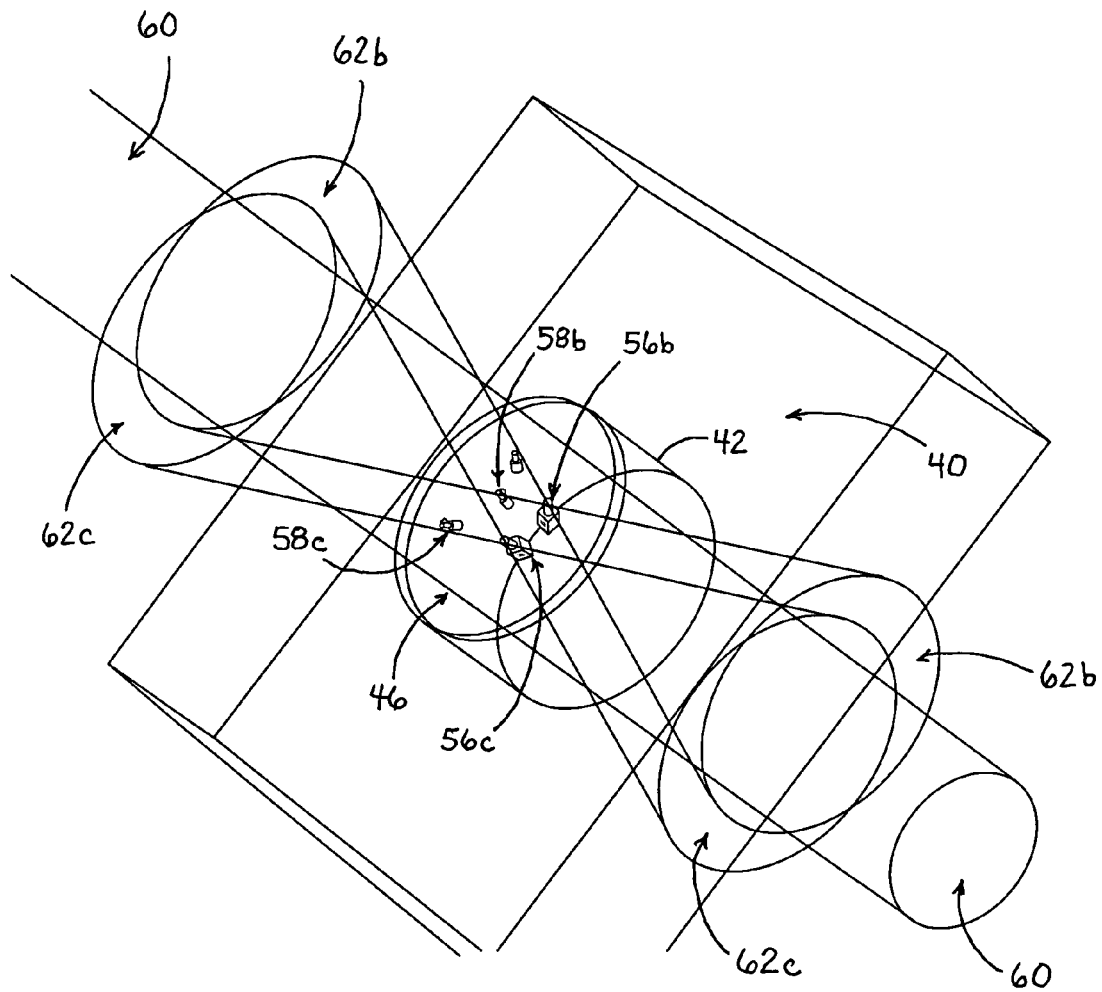
FIG. 13 illustrates that tags on SISAMA antibody pairs bound to target antigen in solution within a well fluoresce (each of the two different SISAMA antibody pairs fluoresces radiation of a different color), but those tags on SISAMA antibody pairs that are bound to scavenger antigen attached to the well wall do not fluoresce.

FIG. 7 is a test well 40 with well wall 42 and scavenger antigens (cylinders) 44. FIG. 8 is a test well 40 with target fluid 46 added having targets and antibody pairs suspended or floating freely in the solution. FIG. 9 is a model of SISAMA antibody pairs (tagged cone pairs) 54*ab* and 54*ac* and antigens (cubes: targets 48*b* and 48*c*; cylinders: scavenger antigens 44). Two types of tagged antibody pairs 54*ab* and 54*ac* and two types of targets 48*b* and 48*c* are depicted (the two types of tagged antibody pairs differ in the type of primary or target antibody that is conjugated with scavenger antibody in each tagged antibody pair). The tag (sphere) 52 is also shown. FIG. 9 also depicts three types of antibodies: circular cone 50*a*, pentagon cone 50*b*, and hexagon cone 50*c*. FIG. 10 illustrates four SISAMA antibody pairs (one of two SISAMA antibody pairs (56*b* and 56*c*) that is suspended in solution is bound to one type of target, and the other of two SISAMA antibody pairs that is suspended in solution is bound to another type of target; two of the four SISAMA antibody pairs (58*b* and 58*c*) are in excess and are bound to scavenger antigens attached to the well wall). Each of the two depicted targets is appropriately bound by a corresponding SISAMA antibody pair, and each of the two depicted excess SISAMA antibody pairs is bound (via its scavenger antibody) to scavenger antigen attached to the well wall. FIG. 11 is a test well 40 through which a detection light beam 60 passes. FIG. 12 illustrates detection light beam 60 missing scavenger antigen 44 (detection light also is missing two tagged SISAMA antibody pairs bound to scavenger antigen 58b and 58c; detection light beam 60 is also illustrated as illuminating each of two tagged SISAMA antibody pairs, each of which is bound to a different target antigen 56b and 56c). FIG. 13 illustrates that tags on SISAMA antibody pairs bound to target antigen in solution within a well fluoresce 62b and 62c (each of the two different SISAMA antibody pairs fluoresces radiation of a different color), but those tags on SISAMA antibody pairs that are bound to scavenger antigen attached to the well wall do not fluoresce.

These and other embodiments of SISAMA include characteristics noted in Table 2.

TABLE 2

Multiple Analytes Methodology Features

| No. | Description of Characteristics of Embodiments |
|---|---|
| 1 | Detection is accomplished with a beam of electromagnetic energy or radiation. The beam is shielded, focused, lased, or controlled in some way so as specifically to avoid illumination of areas where scavenger antigens are located. |
| 2 | Scavenger antigen is obtained or prepared, as is scavenger antibody. The scavenger antibody is conjugated with primary antibody (target antibody) in a SISAMA antibody pair. The scavenger antibody binds to scavenger antigen with a lower binding affinity or avidity than that with which the primary antibody binds to analyte or target. |
| 3 | Scavenger antigen is bound to a portion of the well that is not illuminated by the detection beam but the tagged SISAMA antibody pair-containing test solution yet contacts that portion of the well. |
| 4 | Scavenger antibody and primary antibody (target antibody) are conjugated in such a way that both scavenger antibody and primary antibody cannot or do not bind to their respective goals (i.e., scavenger antigen and target, respectively) at the same time. |
| 5 | The scavenger antigen may be bound to items floating or suspended in the well, but these items have holes, pits, etc., that shadow tagged SISAMA antibody pairs that bind to the scavenger antigen. |
| 6 | Primary antibody (target antibody) is obtained or prepared that binds tightly to the target antigen in order to ensure that SISAMA antibody pairs preferentially bind to targets. |
| 7 | Each different species or kind of target antibody is conjugated with a tag that fluoresces or radiates in a distinguishing way (e.g., at a different wavelength) when struck by the detection beam. The resulting fluorescence or radiation is detected by devices inside or outside the well. |
| 8 | Tagged SISAMA antibody pairs are capable of being dissolved or suspended in the test fluid. |
| 9 | The detection beam can be switched on and off, and yet the signal from the tagged SISAMA antibody pair can be detected during the off periods. |
| 10 | The detection beam can be continuous, and yet signal from the tagged SISAMA antibody pair can be detected as an additional signal. Signal from a well may be separated into individual components (e.g., wavelengths corresponding to signals from different species or kinds of targets) by a photospectrometer or other device (i.e., signal from a well may be analyzed for the identification and quantification of individual species or kinds of targets that are bound by corresponding tagged SISAMA antibody parts). |
| 11 | The detection of the signal from tagged antibodies can be accomplished from a range of angles. |
| 12 | The well has lips that provide additional shadow area to shield the scavenger antigen from the detection beam. |
| 13 | The well has ridges on its walls that provide additional shadow area to shield the scavenger antigen from the detection beam. |
| 14 | The well has depressions or holes that provide additional shadow area to shield the scavenger antigen from the detection beam. |
| 15 | The well bottom does not reflect or scatter the detection beam back into the well. |
| 16 | The test fluid surface may be flat and does not act as a lens. |
| 17 | The test fluid surface may be made flat by contact with a well top. |
| 18 | The test fluid surface may be made flat by avoiding surface tension differences between the fluid and the well. |
| 19 | The test fluid surface may be made flat by filling the well exactly to the neutral fill volume between the meniscus above and below the top of the well. |

Cassette Structures for Testing Fluids and Methods of Use in Immunosorbent Assays In some embodiments, the test cassette includes a plurality of wells with capacity to contain samples and reagent. Ways in which reagent is contained within a well may be used to characterize various embodiments or configurations of the test cassette (for example, as summarized in Table 3).

TABLE 3

Methods for Containment of Reagents

| No. | Containment of Reagent within a Well |
|---|---|
| 1 | Adhered to the wall of the well. |
| 2 | Adhered to sphere(s) or other shape in the well. |

TABLE 3-continued

Methods for Containment of Reagents

| No. | Containment of Reagent within a Well |
|---|---|
| 3 | Absorbed on a sponge or other absorbent material in the well. |
| 4 | In a liquid in the well. |

A well may be divided into a plurality of compartments. A reagent portion of a well (e.g., a portion corresponding to the well portion in the outer sleeve or back plate of the second embodiment of the cassette) may be isolated from the balance of the well to prevent reagent-sample mixing until mixing is desired.

Well portion volumes may be carefully controlled in order to permit use of the known volume of a well portion for estimating or measuring the volume or amount of a reagent or other liquid sample occupying the well portion. Such estimates or measurements may be helpful in calculating the concentration of a compound (e.g., an analyte in a sample) In a liquid in the well.

Wells may be kept free of sample fluid until desired. Sample may be introduced into wells through capillary action, injection, pouring, suction or other means known to those skilled in the art (e.g., by submersion).

A clear pane may cap a well at one or both ends. If a well has a clear pane at both ends, light may pass completely through the well. Pane surfaces and other well surfaces (or non-surface materials) may be a certain color and allow light of only certain wavelength(s) to reflect from (or pass through) them. In particular, well surface and non-surface materials may be completely transparent and allow light to pass through wells in any direction.

The cassette may have an identifying mark or marks [e.g., bar code, radio frequency identification (WID) tag, detents ("click-stops"), or other marks known to those skilled in the art] that allow a detector to identify a cassette that has been placed in the detector.

The Detector

In some embodiments, the detector simultaneously emits a light consisting of range(s) of wavelengths, i.e., of one or several different spectra. The detector may also emit only one wavelength, or a plurality of different wavelengths, of light over programmed time period(s). Light typically shines into, or through, a well during testing.

In some embodiments, the detector includes a plurality of light receivers. These may capture light that has traveled through reagent, sample or mixtures of reagent and sample. In some embodiments, the detector may include only one light receiver; this receiver may be capable of capturing light reflected from, or transmitted through, one or multiple wells.

A light receiver usually is connected to a device that can process data (e.g., match a calorimetric measurement from a table of potential readings in order to identify, quantify, or both identify and quantify, analyte in a tested fluid).

In some embodiments, the detector includes a man machine interface (MMI) that allows an operator to control the detector as well as to save and download data generated from analysis using the cassette. This MMI may be integral to the detector or be part of a separate computer connected by a direct communication cable or a network link to the detector.

A First Embodiment of the Test Cassette/Detector

In a first embodiment, a cassette has a plurality of (e.g., more than 100) wells. The cassette includes three parts: a generally circular reagent well plate, a central water or sample well plate, and a generally circular cover. Well bottoms of the reagent well plate are opposite the bulk of the rest of the cassette. The wells or well portions of the other two plates transverse or pass through those plates. All three plates are held together tightly at the center, and yet they may be caused to rotate relative to each other about the center (while permitting various wells to remain sealed).

Some wells may be used for calibration purposes (e.g., for comparing transmitted or reflected light values to expected values).

In some configurations, the cover and the reagent well plates are made of an optically clear plastic.

After reagents are loaded into reagent wells or reagent well portions, the central water (or sample) well plate may be rotated or affixed relative to the reagent well plate in such a way that the wells or well portions of the two plates do not align.

The cover plate may be rotated or affixed to prevent any water or other sample fluid from entering wells or well portions of the central plate until the cover plate is rotated into a well-alignment position. When the cover has been removed or turned to a position where holes in the cover are aligned with wells or well portions of the central plate, water or other liquid sample can enter and fill wells or well portions of the central plate (i.e., samples can be taken). The cover plate may then be replaced or further turned so that samples are sealed within the wells or well portions.

When a test is to be run, the reagent well plate may be rotated so that wells or well portions of the reagent well plate align with wells or well portions of the central plate. For each aligned well, reagent can then mix with a corresponding sample. Light also then may be allowed to pass through the cover overlying a sample well, through sample of an aligned central plate well portion and through reagent of an aligned reagent plate well portion, even as sample mixes with reagent. If the sample-reagent reaction may be assayed or measured through a calorimetric means, detected and measured light characteristics can then be translated into data (e.g., colorimetric data may be used to calculate analyte concentration in a sample).

In some configurations, the reagent well or reagent well portion is filled nearly to capacity. A small void or gas space may form (i.e., a bubble may form) when a reagent well or reagent well portion is aligned with a sample well or sample well portion. This bubble may provide space to facilitate or permit mixing liquid sample (e.g., a water-dissolved sample) and reagent by agitation.

In some configurations, a well or well portion may be larger in diameter at one end versus another end. If a void or gas space (i.e., a bubble) forms at a larger-diameter end of a well or well portion, the bubble's small size relative to the well diameter may permit light from a detector to pass through the well in a path that does not encounter the bubble.

The detector may emit lights of various wavelengths that pass through a cassette. One device that converts light to an electrical or digital signal (such as a charge coupled device or CCD) may be used to collect light after it has passed through a well or wells of a cassette.

When a cassette is snapped into a detector, the detector reads the barcode, WID tag, or other identifying mark(s) and determines the type(s) of tests that may be executed. The detector then proceeds through a preprogrammed sequence of light emission and capture and data collection steps (e.g., for the collection of calorimetric data). Specialized software is used in the collection and analysis of data. Raw collected data, as well as results from analyzing the collected data, are saved (optionally with date, time, program parameters, etc.).

The saved data and results may be reviewed immediately or recalled for review at a later time.

A Second Embodiment of the Test Cassette/Detector

In a second embodiment, a cassette has a plurality of (e.g., more than 100) wells. The cassette includes two major parts: an outer sleeve or back plate and an inner or front plate. Each part preferably includes wells or well portions. In some configurations, well bottoms are clear (well bottoms may be molded during formation of well walls or affixed after well walls are formed).

As in the previously described first embodiment, some wells or well portions may be used for calibration purposes (e.g., for comparing transmitted or reflected light values to expected values).

In some configurations, the outer sleeve or back plate includes reagent wells or reagent well portions and fill channels. The inner or front plate includes wells or well portions for water or other sample liquid(s). In one configuration, wells or well portions of the two plates are not aligned and reagent is sealed (with a small gas bubble) in each well or well portion of the outer sleeve or back plate.

In some configurations, a cassette of the second embodiment includes a third major part: a "trigger" or plunger. This trigger or plunger may be spring loaded. Movement of the trigger seals (or opens) one or more entry ports (e.g., along a side of the cassette) to one or more wells.

When the trigger is depressed in some configurations, ports (e.g., a top port and a bottom port) are opened on the side of the cassette's outer sleeve. These ports may connect to runners or channels that in turn connect to wells or well portions of the front or inner plate. Paths for movement of water (or other liquid sample or displaced air or other gas) between runners or channels of the outer sleeve to wells or well portions of the cassette's inner or front plate may thus be opened. This provides a path for water or other liquid sample to enter, for example, through the bottom port, continue through runners or channels of the outer sleeve, and fill into wells or well portions of the inner or front plate. In this configuration, displaced air or other gas may leave the cassette through the top port.

When a cassette is filled and the operator is ready to test liquid sample(s), the inner or front plate may be pushed so as to align sections of reagent well or well portions of the outer sleeve or back plate with water or sample wells or well portions in the cassette's inner or front plate. Agitating or shaking the cassette permits reagent and liquid sample to mix (a residual bubble may provide space to facilitate mixing).

As noted for the previously described first embodiment, a detector for use with a cassette of this second embodiment may emit (or capture or both emit and capture) lights of various wavelengths. A detector (or other device) may be used to capture light that has passed through, or reflected from, or passed through and reflected from, one or more wells of this second embodiment.

Water or other liquid sample may be added to wells or well portions of the cassette's inner or front plate in various ways, including: 1) depressing the trigger and injecting sample fluid into wells; or 2) submerging the cassette in water or other liquid sample and then depressing the trigger in order to release air from the wells and to permit water or other sample liquid to fill the wells or well portions of the inner or front plate. Water or other liquid sample may be added to multiple cassettes at the same time but from various depths (e.g., of larger volumes of water or other liquid sample) in order to obtain, for example, a depth profile of the water or other liquid sample.

After the cassette is snapped into the detector, the detector reads the barcode, RFID tag or other identifying mark(s) and determines the type(s) of tests that may be executed. The detector may then proceed through a preprogrammed sequence of light emission(s), light capture(s) and other data extraction and analyses. As noted previously for configurations of the first embodiment, specialized software is used in the collection and analysis of data. Raw collected data, as well as results of collected data analysis, are saved (optionally with date, time, program parameters, etc.). Also as previously noted for configurations of the first embodiment, the saved data and results may be reviewed immediately or recalled for review at a later time.

A Third Embodiment of the Test Cassette/Detector

A third embodiment includes a detector that may contain a magazine of cassettes. The detector (or cassette/detector system) may process cassettes of the magazine serially or as a group (and, in some configurations, with little or no human intervention). The detector could, as pre-programmed, obtain a reading from a sample, analyze it, and then: a) send data to a user, b) store the data for later retrieval, or c) accomplish both. This third embodiment could also be set up so that the system only cycled when a sample was entered into the system.

Figure 14:
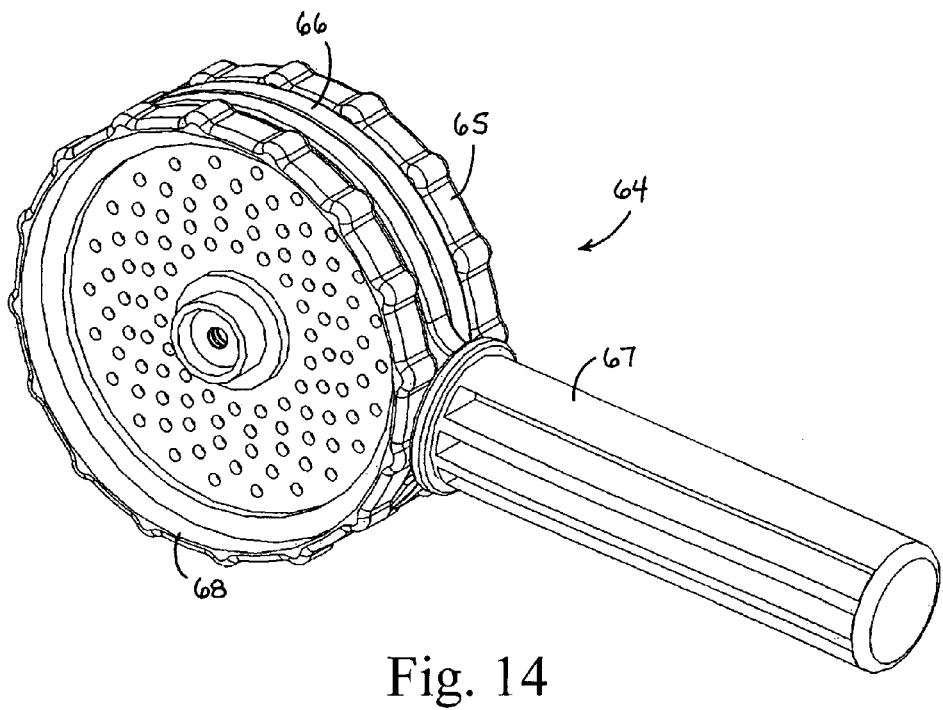
FIG. 14 is a cassette structure for testing fluids.
Figure 15:
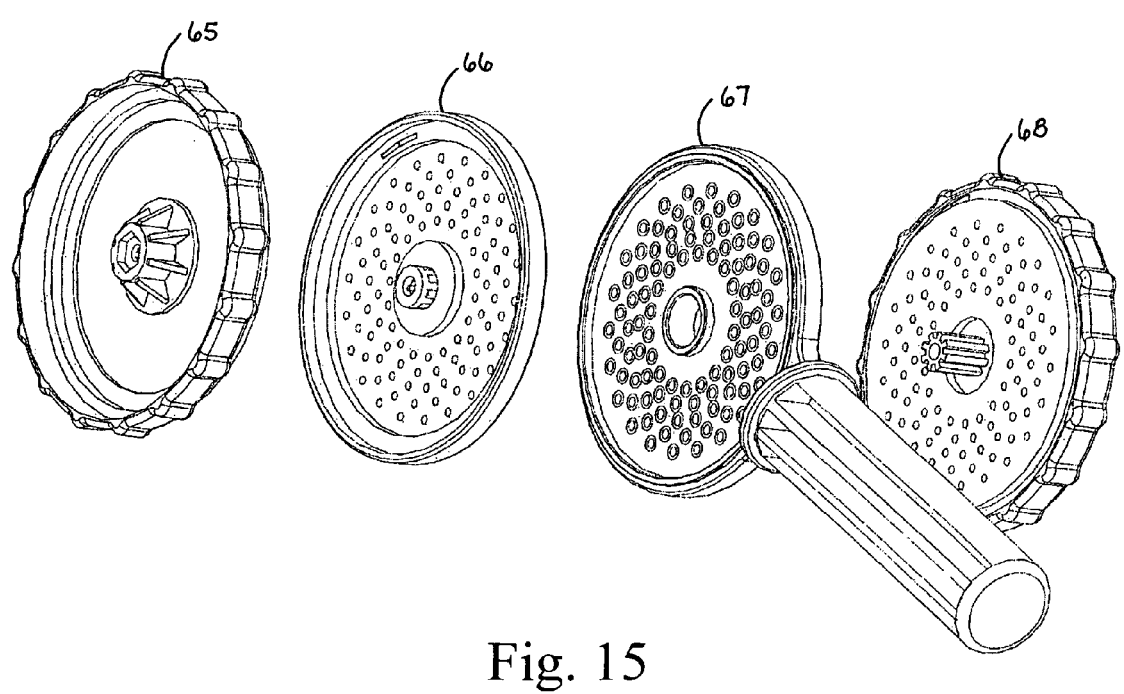
FIG. 15 is a disassembled cassette structure for testing fluids.
Figure 16:
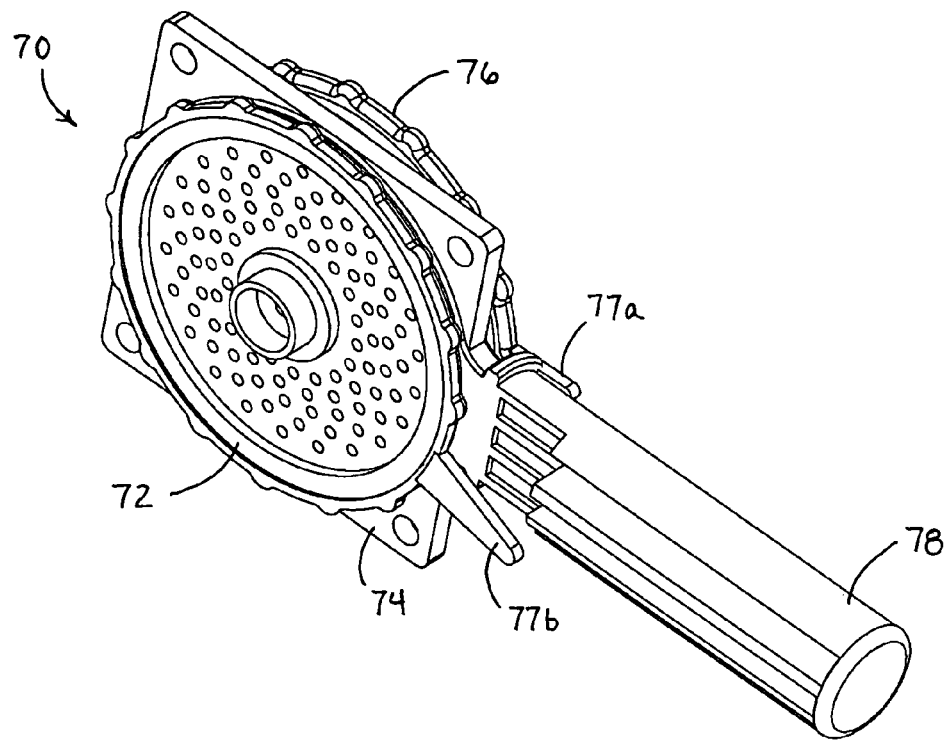
FIG. 16 is an oblique view of a first embodiment of a cassette for testing fluids. The sample wells are in a central plate (generally square with a paddle handle). Reagent wells or reagent portions of wells (not visible) are present in a generally circular reagent well plate attached on the far side. A generally circular cover plate is attached on the near side of the central plate. This figure also depicts small "handles" that facilitate rotating the cover plate disk and reagent well plate disk. These handles could be alternatively be formed as teeth, sprockets, ratchets, etc.
Figure 17:
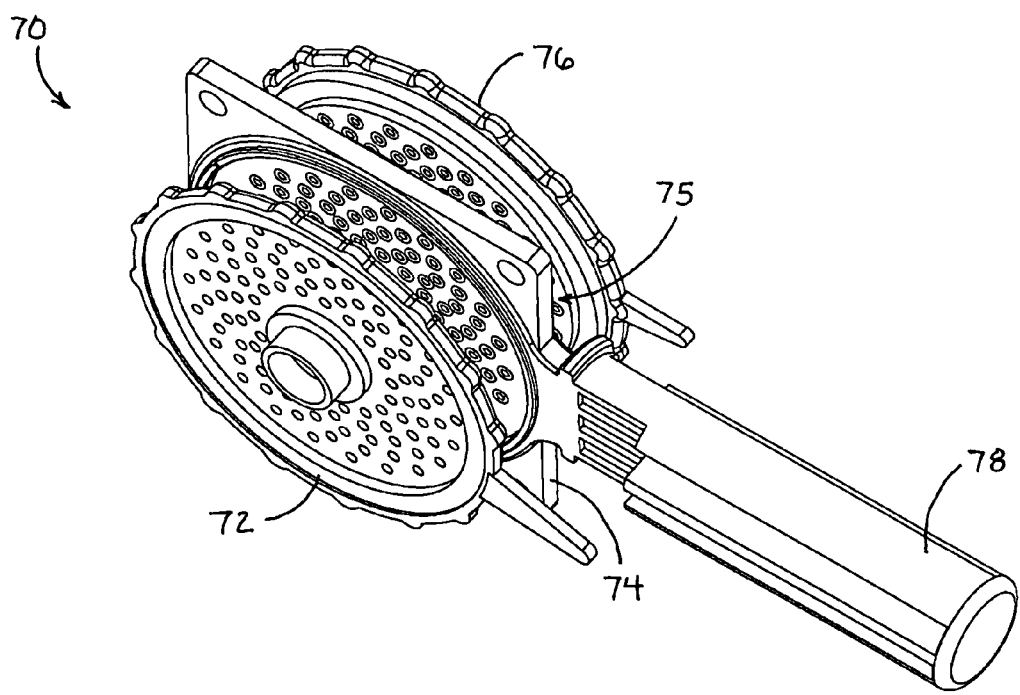
FIG. 17 is an exploded view of this first cassette embodiment such that wells or well portions may be better viewed. Circular ridges are depicted around the well circumferences. These ridges are part of seals that isolate the wells or well portions.
Figure 18:
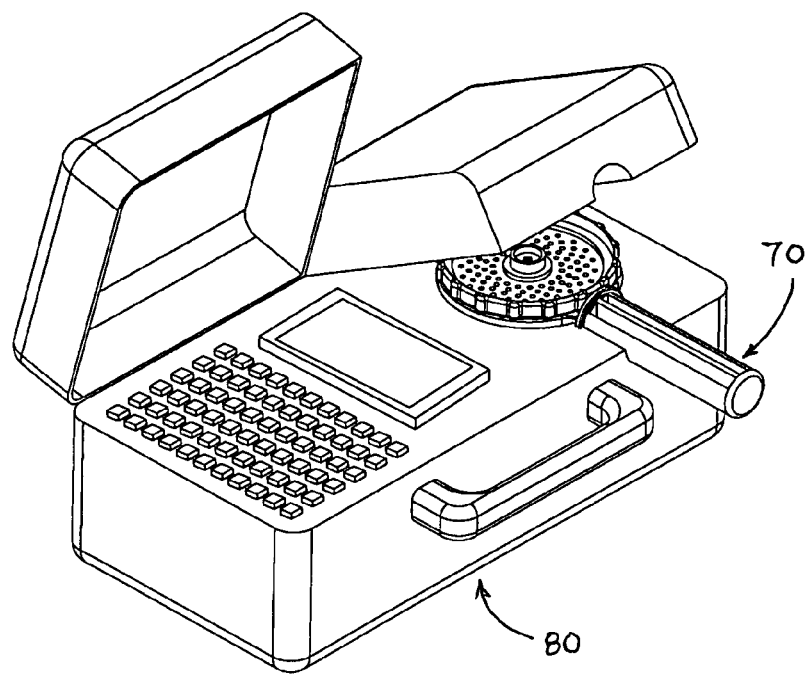
FIG. 18 depicts a cassette similar to this first cassette embodiment in a portable, self-contained detector.
Figure 19:
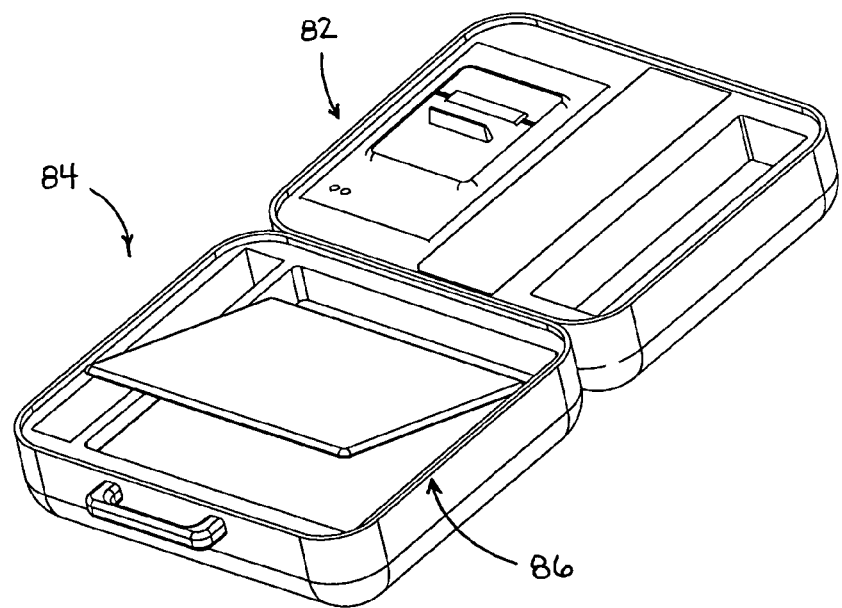
FIG. 19 depicts a simple detector connected to a laptop wherein the detector and laptop are held in a commercial "briefcase;"

FIG. 14 is a cassette structure for testing fluids. FIG. 15 is a disassembled cassette structure for testing fluids. FIG. 16 is an oblique view of a first embodiment of a cassette 70 for testing fluids. The sample wells are in a central plate 74 (generally square with a paddle handle 78). Reagent wells or reagent portions of wells (not visible) are present in a generally circular reagent well plate attached on the far side. A generally circular cover plate 72 is attached on the near side of the central plate 74. This figure also depicts small "handles" 77a and 77b that facilitate rotating the cover plate disk and reagent well plate disk 76. These handles could be alternatively formed as teeth, sprockets, ratchets, etc. FIG. 17 is an exploded view of this first cassette embodiment 70 such that wells or well portions may be better viewed. Circular ridges 75 are depicted around the well circumferences. These ridges are part of seals that isolate the wells or well portions. FIG. 18 depicts a cassette 70 similar to this first cassette embodiment in a portable, self-contained detector 80. FIG. 19 depicts a simple detector 82 connected to a laptop 86 wherein the detector and laptop are held in a commercial "briefcase" 84.

Figure 20:
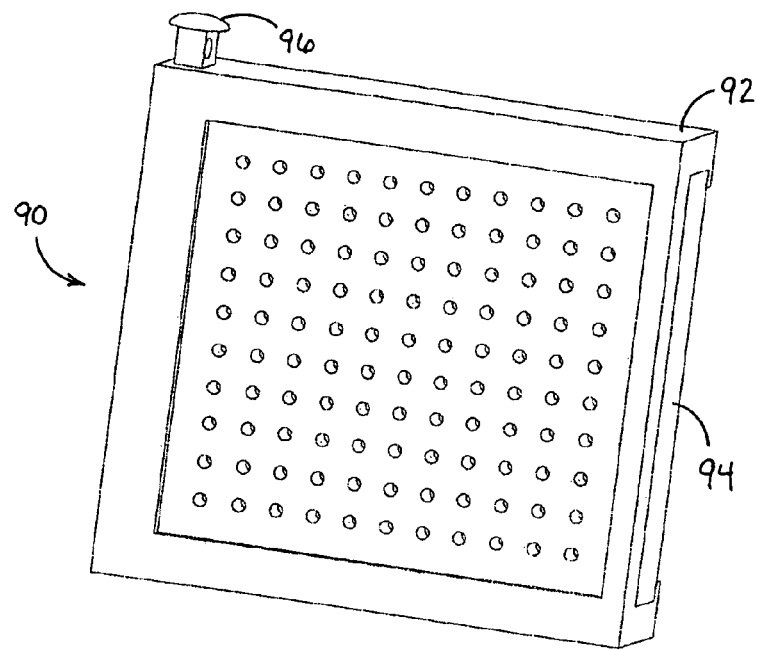
FIG. 20 is a largely broad side view of a second embodiment of a cassette for testing fluids.
Figure 21:
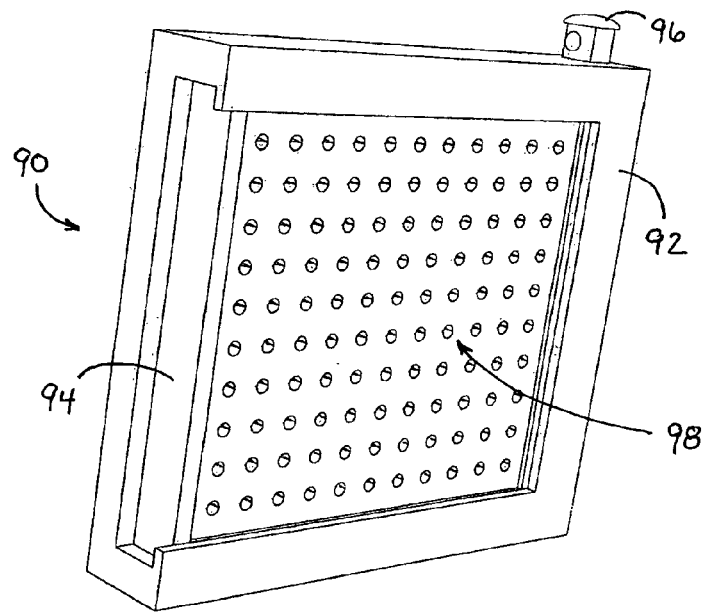
FIG. 21 is an angled side view of this second embodiment depicting sample wells or well portions in an inner or front plate.
Figure 22:
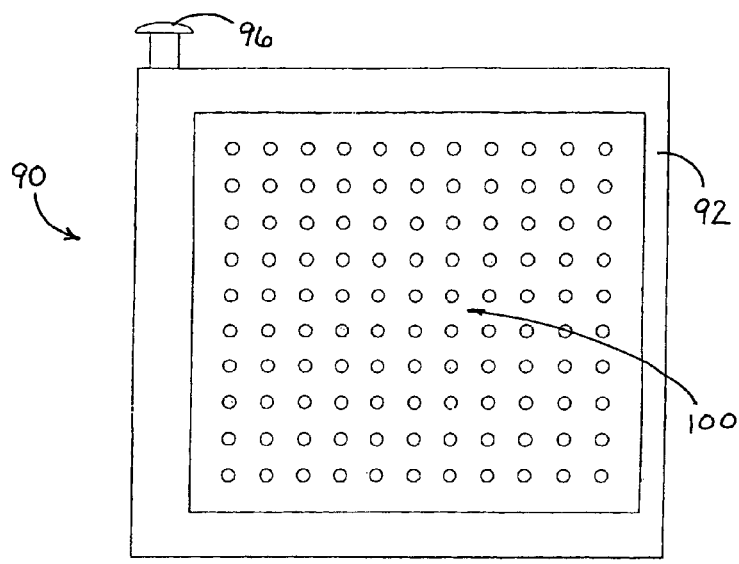
FIG. 22 is a flat-on broad side view of this second embodiment of a cassette for testing fluids. Reagent wells or reagent well portions of wells are visible in the outer sleeve or back plate.
Figures 23A, 23B:
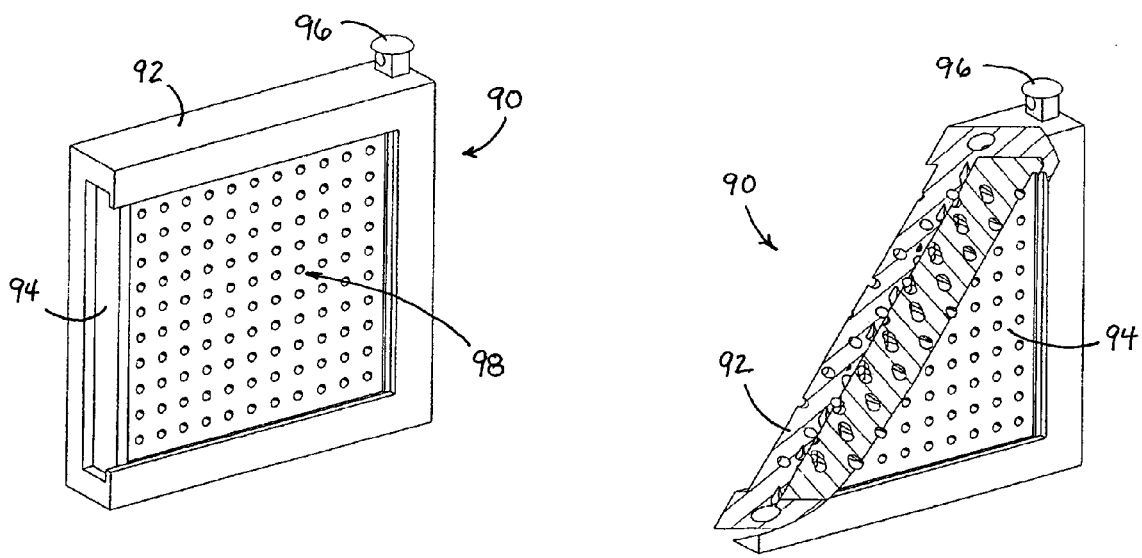
FIGS. 23A and 23B diagram a diagonal cut-away view of this second embodiment of a cassette for testing fluids.
Figure 24E:
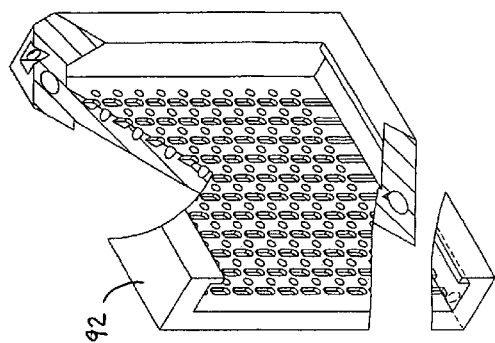
FIGS. 24A-24E diagram further side and cut-away views of an outer sleeve or back plate of this second embodiment of a cassette for testing fluids. A thin inset covers the outer end of reagent wells or reagent well portions in the narrow side views of the outer sleeve or back plate. This inset forms a pane or bottom for reagent wells or reagent well portions in the outer sleeve or back plate.
Figure 24B:
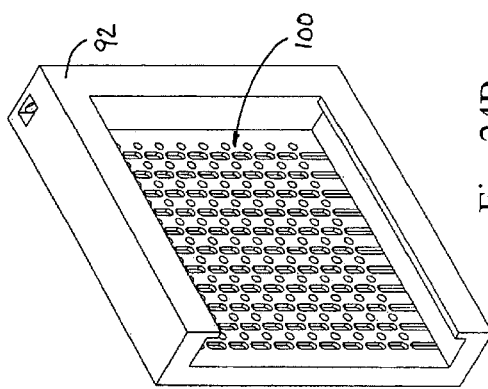
Figure 24D:
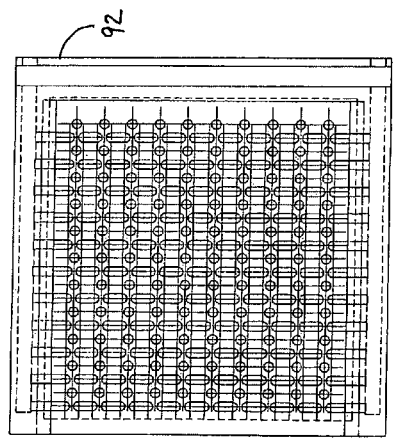
Figure 24A:
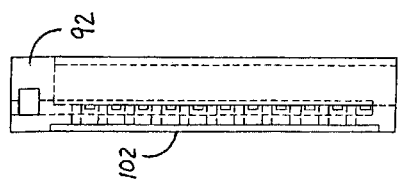
Figure 24C:
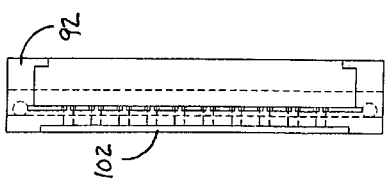
Figure 25E:
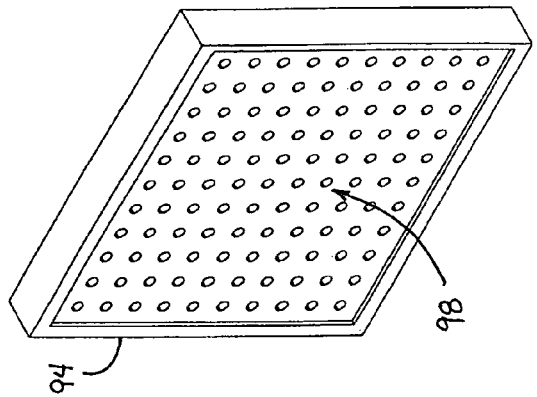
FIGS. 25A-25E diagram side and angle views of an inner or front plate of this second embodiment of a cassette for testing fluids. Space for a thin inset to cover the wells or well portions for water or sample is diagrammed in the narrow side views, as it is also diagrammed in the front-on, broad side view and the angled view of the inner or front plate. This inset forms a pane or opposite bottom for wells or well portions for water or sample in the inner or front plate.
Figure 25D:
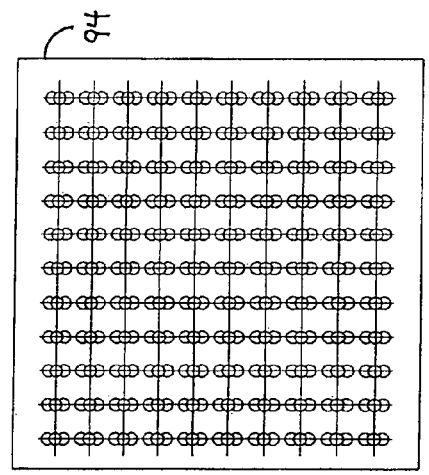
Figure 25C:
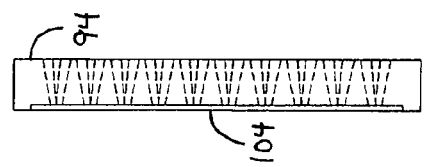
Figure 25A:
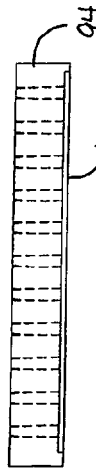
Figure 25B:
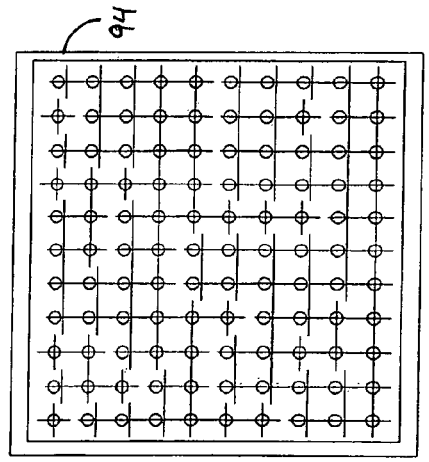
Figure 26D:
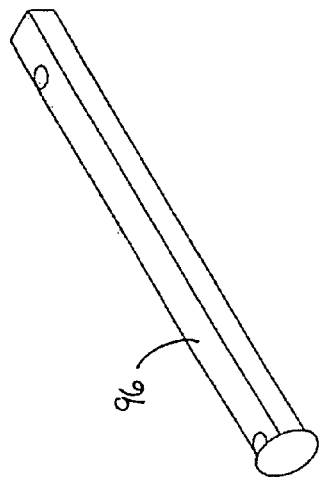
FIGS. 26A-26D diagram a trigger or plunger of this second embodiment of a cassette for testing fluids.
Figure 26C:
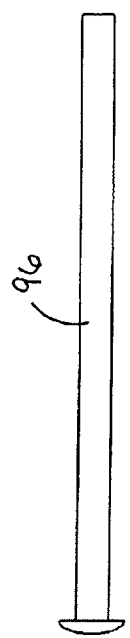
Figure 26A:
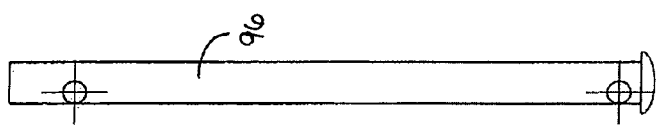
Figure 26B:
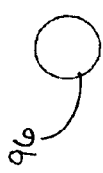

FIG. 20 is a largely broad side view of a second embodiment of a cassette 90 for testing fluids having an outer sleeve/back plate 92, an inner/front plate 94, and a trigger/plunger 96. FIG. 21 is an angled side view of this second embodiment depicting sample wells or well portions 98 in an inner or front plate 94. FIG. 22 is a flat-on broad side view of this second embodiment of a cassette 90 for testing fluids. Reagent wells or reagent well portions of wells 100 are visible in the outer sleeve or back plate 92. FIGS. 23A and 23B diagram a diagonal cut-away view of this second embodiment of a cassette 90 for testing fluids. FIGS. 24A-24E diagram further side and cut-away views of an outer sleeve or back plate 92 of this second embodiment of a cassette 90 for testing fluids. A thin inset 102 covers the outer end of reagent wells or reagent well portions 100 in the narrow side views of the outer sleeve or back plate 92. This inset forms a pane or bottom for reagent wells or reagent well portions in the outer sleeve or back plate. FIGS. 25A-25E diagram side and angle views of an inner or front plate 94 of this second embodiment of a cassette for testing fluids. Space for a thin inset 104 to cover the wells or well portions for water or sample is diagrammed in the narrow side views, as it is also diagrammed in the front-on, broad side view and the angled view of the inner or front plate. This inset forms a pane or opposite bottom for wells or well portions 98 for water or sample in the inner or front plate. FIGS. 26A-26D diagram a trigger or plunger 96 of this second embodiment of a cassette 90 for testing fluids.

Figure 27:
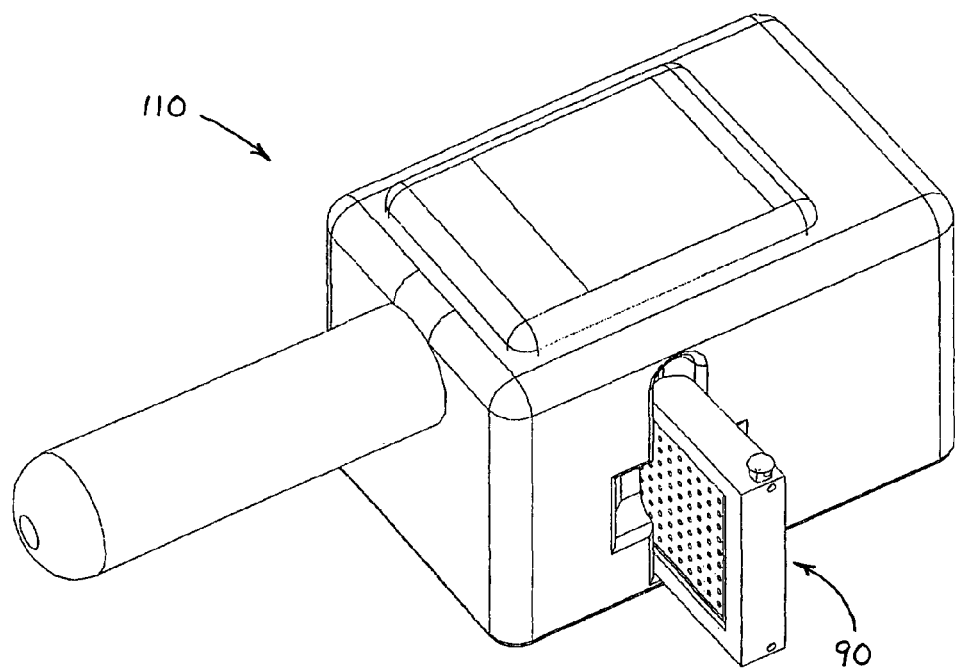
FIG. 27 depicts a detector into which this second embodiment of a cassette for testing fluids is inserted.
Figure 28:
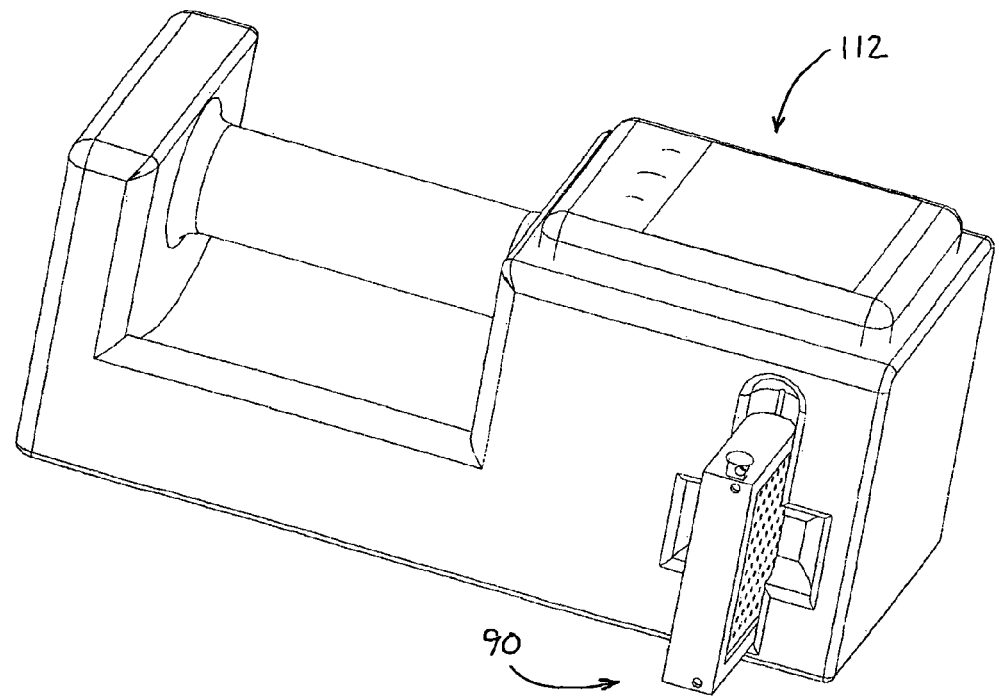
FIG. 28 depicts another embodiment of a detector into which this second embodiment of a cassette for testing fluids is inserted.

FIG. 27 depicts a detector 110 into which this second embodiment of a cassette 90 for testing fluids is inserted. FIG. 28 depicts another embodiment of a detector 112 into which this second embodiment of a cassette 90 for testing fluids is inserted. FIGS. 29A-29C diagram this second embodiment of a cassette 90 for testing fluids in a closed, ready-to-use position. The air outlet port 120 and runner (at the top of the cassette and plunger) are not aligned, and neither is the water or sample inlet port 122 and runner (at the bottom of the cassette and plunger). The cassette is in a sealed, closed, ready to use position. The holes in the front and back pieces are not aligned and the reagent is captured in the back piece. This section view shows the air outlet runner (at top) and the water inlet runner (at bottom) cut off by the plunger 96.

FIGS. 30A-30C diagram this second embodiment of a cassette 90 for testing fluids in a sample-taking position. Both the air outlet port 120 and runner (at the top of the cassette and plunger) and the water or sample inlet port 122 and runner (at the bottom of the cassette and plunger) are aligned. Consequently, water or sample from the cassette's exterior can fill wells in the inner or front plate 94 with water or sample fluid. But the reagent wells or reagent well portions in the outer sleeve or back plate are not aligned with wells or well portions of water or sample in the cassette's inner or front plate. Consequently, reagent remains captured in the outer sleeve or back plate. The holes in the front and back are not aligned and the reagent remains captured in the back piece. With the plunger 96 depressed, the air outlet runner (at top) and the water inlet runner (at bottom) are now open to the sample media. This allows the sample wells in the front piece to fill with the sample fluid.

FIGS. 31A-31C diagram this second embodiment of a cassette 90 for testing fluids in an analysis position. The trigger or plunger 96 has returned to its original position (again, the air outlet port 120 and runner at the top of the cassette and plunger are not aligned, and neither are the water or sample inlet port 122 and runner at the bottom of the cassette and plunger), and water or sample fluid has been captured in the cassette. When a researcher or an operator is ready to proceed with sample analysis, the researcher or operator may snap or shift the inner or front plate 94 so that the reagent wells or reagent well portions of the outer sleeve or back plate 92 align, or connect, with the wells or well portions of water or sample in the inner or front plate (to the right in this view). This changes the alignment of the wells from the sampling runners to being aligned with the reagent wells. A small bubble left in the reagent wells causes complete mixing when the cassette is shaken (yet stays out of the way in the wide part of the sample well to allow clear detection through the now complete well by the detector).

Figure 32:
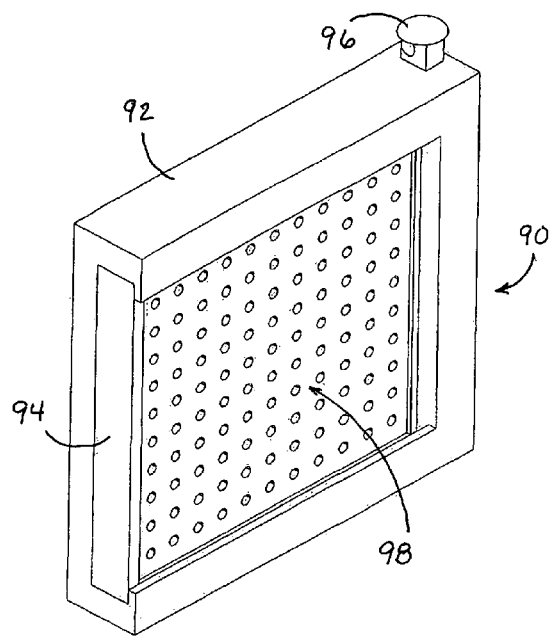
FIG. 32 is another angled side view of this second embodiment of a cassette for testing fluids. The trigger or plunger is in its original position.
Figure 33:
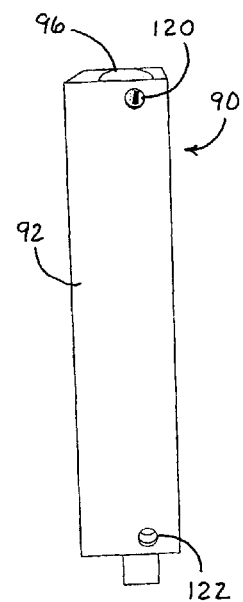
FIG. 33 is a narrow side view of this second embodiment of a cassette for testing fluids. The trigger or plunger is depressed.
Figure 34:
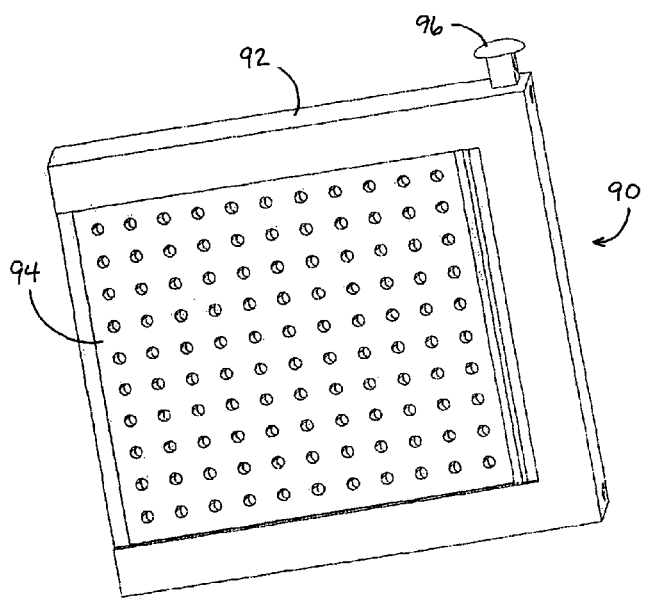
FIG. 34 is a largely broad side view of this second embodiment of a cassette for testing fluids. The trigger or plunger is in its original position.

FIG. 32 is another angled side view of this second embodiment of a cassette 90 for testing fluids. The trigger or plunger 96 is in its original position. FIG. 33 is a narrow side view of this second embodiment of a cassette 90 for testing fluids. The trigger or plunger 96 is depressed. FIG. 34 is a largely broad side view of this second embodiment of a cassette 90 for testing fluids. The trigger or plunger 96 is in its original position.

Although various embodiments of the method and apparatus of the present invention have been illustrated in the accompanying Drawings and described in the foregoing Detailed Description, it will be understood that the invention is not limited to the embodiments disclosed, but is capable of numerous rearrangements, modifications and substitutions without departing from the spirit of the invention as set forth herein.

I claim:

1. A method for immunologically analyzing a sample for a single analyte comprising the steps of:
   introducing scavenger antigens into a well and binding them to the well;
   introducing test fluid into the well to form a solution, the step of introducing test fluid comprising the steps of:
      introducing tagged antibodies into the well;
      introducing target antigens into the well;
   agitating the solution in the well to allow binding to occur first between the tagged antibodies and the target antigens and second, in the absence of sufficient target antigens, between the tagged antibodies and the scavenger antigens; and
   immediately after agitating the well and while retaining the solution in the well, detecting tagged antibodies bound to target antigens that remain suspended in the solution in the well.

2. A method for immunologically analyzing a sample for multiple analytes comprising the steps of:
   introducing scavenger antigens into a well and binding them to the well;
   introducing test fluid into the well to form a solution, the step of introducing test fluid comprising the steps of:
      introducing bound pairs of scavenger antibodies and tagged primary antibodies into the well;
      introducing target antigens into the well;
   agitating and retaining the solution in the well to allow binding to occur first between the tagged primary antibodies and the target antigens and second, in the absence of sufficient target antigens, between the scavenger antibodies and the scavenger antigens; and
   immediately after agitating the well and while retaining the solution in the well, detecting tagged antibodies bound to target antigens that remain suspended in the solution in the well.

* * * * *